(12) United States Patent
Bender et al.

(10) Patent No.: US 9,078,485 B2
(45) Date of Patent: Jul. 14, 2015

(54) SPORT PERFORMANCE MONITORING APPARATUS INCLUDING A FLEXIBLE BOOT PRESSURE SENSOR COMMUNICABLE WITH A BOOT PRESSURE SENSOR INPUT, PROCESS AND METHOD OF USE

(71) Applicants: Chris Norcross Bender, Reno, NV (US); Roger S. Bishop, Dayton, NV (US); Kay Daniel Netter, Reno, NV (US)

(72) Inventors: Chris Norcross Bender, Reno, NV (US); Roger S. Bishop, Dayton, NV (US); Kay Daniel Netter, Reno, NV (US)

( * ) Notice: Subject to any disclaimer, the term of this patent is extended or adjusted under 35 U.S.C. 154(b) by 340 days.

(21) Appl. No.: 13/652,421

(22) Filed: Oct. 15, 2012

(65) Prior Publication Data
US 2013/0093588 A1    Apr. 18, 2013

Related U.S. Application Data

(60) Provisional application No. 61/547,614, filed on Oct. 14, 2011, provisional application No. 61/713,464, filed on Oct. 12, 2012.

(51) Int. Cl.
| | | |
|---|---|---|
| *G08B 21/00* | (2006.01) | |
| *A43B 3/00* | (2006.01) | |
| *G09B 19/00* | (2006.01) | |
| *A43B 5/04* | (2006.01) | |

(52) U.S. Cl.
CPC ............. *A43B 3/0015* (2013.01); *A43B 3/0021* (2013.01); *A43B 5/0415* (2013.01); *G09B 19/0038* (2013.01)

(58) Field of Classification Search
CPC ............................ A43B 13/181; A43B 3/0005

USPC .............. 340/539.11, 539.22, 539.26, 573.7; 36/132
See application file for complete search history.

(56) References Cited

U.S. PATENT DOCUMENTS

| | | | |
|---|---|---|---|
| 3,644,919 A | | 2/1972 | Mathauser |
| 4,516,110 A | | 5/1985 | Overmyer |
| 4,583,305 A | * | 4/1986 | Miyamoto .................. 36/117.9 |
| 4,703,445 A | | 10/1987 | Dassler |
| 5,005,140 A | | 4/1991 | Havriluk |
| 5,221,088 A | | 6/1993 | McTeigue et al. |
| 5,295,085 A | | 3/1994 | Hoffacker |
| 5,372,365 A | | 12/1994 | McTeigue et al. |
| 5,877,687 A | | 3/1999 | Bernard et al. |

(Continued)

OTHER PUBLICATIONS

International Search Report and Written Opinion of the International Searching Authority for International Application PCT/US2012/060318, mailed Jan. 7, 2013.

(Continued)

*Primary Examiner* — Mark Rushing
(74) *Attorney, Agent, or Firm* — Holland & Hart LLP

(57) ABSTRACT

A sports monitoring system and method. One disclosed system can be used during skiing and includes a controller transceiver that can be hand held, two ski boot pressure monitor/transmitters, and earphones connectable to the controller/transceiver. The system can be used to provide, through the earphones, sound indicative of pressure applied or not applied by a skier toward a portion of a boot while skiing. The system may also include a proximity sensor mounted within one of the ski boot pressure monitor/transmitters. The system can thereby provide sound responsive to the proximity detector's detection of one boot being at or not at a distance, or within or outside of a distance range, with respect to the other boot.

1 Claim, 17 Drawing Sheets

(56) References Cited

U.S. PATENT DOCUMENTS

| | | | |
|---|---|---|---|
| 5,878,378 A | 3/1999 | Brommer et al. | |
| 6,266,623 B1 | 7/2001 | Vock et al. | |
| 6,377,178 B1 | 4/2002 | DeToro et al. | |
| 6,384,729 B1 | 5/2002 | Plotkin | |
| 6,533,296 B1 | 3/2003 | Farraday | |
| 6,807,869 B2 | 10/2004 | Farringdon et al. | |
| 7,188,439 B2 | 3/2007 | Dibenedetto et al. | |
| 7,512,515 B2 | 3/2009 | Vock et al. | |
| 7,930,131 B2 | 4/2011 | Ridenour et al. | |
| 2003/0014210 A1 | 1/2003 | Vock et al. | |
| 2005/0038626 A1 | 2/2005 | Flentov et al. | |
| 2006/0248749 A1* | 11/2006 | Ellis | 36/28 |
| 2007/0001106 A1 | 1/2007 | Schmidt et al. | |
| 2007/0006489 A1 | 1/2007 | Case, Jr. et al. | |
| 2007/0061107 A1 | 3/2007 | Vock et al. | |
| 2007/0208530 A1 | 9/2007 | Vock et al. | |
| 2011/0131012 A1 | 6/2011 | Czaja et al. | |

OTHER PUBLICATIONS

Popular Science, Bluetooth 4.0, Circuit Training, The first exercise tracker that doubles as a real-time coach, Jun. 2012.

vLINK Advanced Racing Computers, The vLink Racing Computer, Real Measurement for Real Improvement.

Julia Schwarz, Pressure Sensitive Ski Boots, Final Report, Gadgets in HCI, Spring 2010.

* cited by examiner

SPORT PERFORMANCE MONITORING APPARATUS INCLUDING A FLEXIBLE BOOT PRESSURE SENSOR COMMUNICABLE WITH A BOOT PRESSURE SENSOR INPUT, PROCESS AND METHOD OF USE

RELATED APPLICATIONS

The present application for patent claims priority to U.S. Provisional Application No. 61/547,614 entitled "SPORT PERFORMANCE MONITORING APPARATUS, PROCESS AND METHOD OF USE," filed Oct. 14, 2011 and U.S. Provisional Application No. 61/713,464 entitled "SPORT PERFORMANCE MONITORING APPARATUS, PROCESS AND METHOD OF USE," filed Oct. 12, 2012, both of which Provisional Applications are hereby expressly incorporated by reference in their entirety including the source code appendix of U.S. Provisional Application No. 61/713,464.

COPYRIGHT NOTICE

A portion of the disclosure of this patent document contains or may contain material subject to copyright protection. The copyright owner has no objection to the photocopy reproduction of the patent document or the patent disclosure in exactly the form it appears in the Patent and Trademark Office patent file or records, but otherwise reserves all copyright rights.

FIELD OF INVENTION

The present invention relates to sport training devices. In one particular embodiment, pressure distribution and/or limb proximity are monitored in real time.

BACKGROUND

The typical ski turn is a collection of decision points that the skier makes starting with where to turn. Once that decision is made, a cascade of other decisions and actions occur dependant on when that first decision was made.

In order to properly initiate a ski turn, varying degrees of forward pressure are exerted against the tongue of a ski boot. In one common turn in ski racing for example, the skier first exerts neutral forward pressure, followed by increasing continual forward pressure in varying degrees. The proper timing and maintenance of forward pressure can, depending on skiing conditions, improve the shape of the turn, the control of the turn, the speed of the skier, the direction of the turn, the quickness of edge transitions and many other nuances of a ski turn. These factors apply in varying degrees to varying ski conditions and circumstances such as recreational, racing, powder, groomed, ice, and bump or mogul skiing as well as many other types of skiing and ski conditions. Teaching and training proper form with respect to ski turns is particularly difficult due to both the difficulty in externally observing forward or other pressure and ski proximity, as well as the inability to communicate the form break to the skier at the moment the problem occurs.

One mechanical strategy of attempting to compensate for improper pressure distribution and ski proximity involves changing the physical shaping of skis. Shaping of the ski does make skiing easier, but it does not by itself solve the full range of issues that result from improper pressure distribution and ski proximity. For example, in ski racing, if the skier is not leaning forward sufficiently, a turn can be initiated, but the racer can lose edge control as a result, skidding and losing speed or time through the course as a result. This loss of control in one turn can cause further loss of control in one or more subsequent turns as well as complete loss of control and exit from the race course. The difference between a correct turn and a bad turn is often a direct result of whether or not the skier is leaning forward sufficiently and applying sufficient forward pressure to the portions of the ski boots abutting the skier's lower shin as well as by whether the skis are appropriately spaced, or in some cases (e.g., bump skiing) not spaced, from one another Various electronic systems have been provided to try to provide real-time feedback to the skier. These systems have typically used small, spot electronic sensors selectively positioned by the skier in order obtain response. These systems have proven to be too inaccurate due to their small size and inability to detect leg pressure across the surface of the tongue of the ski boot Additional disadvantages of the use of electronic spot sensors included the cost of electronic sensors, the use of multiple sensors to obtain accurate monitoring in a single ski boot, frequent adjustment to the location of the sensor within the boot in order to obtain the most accurate monitoring, and compromised durability due to susceptibility to weather conditions and friction.

Yet another disadvantage of these electronic systems is that have not provided any detection of ski proximity. In certain types of skiing conditions and in ski racing in particular, the feet should be sufficiently independent and the hips should not be locked in position with respect to the legs and feet. Further, when the feet are sufficiently separated and distanced from one another, the skier can generate edge pressure without tilting the body to one side. If a skier is notified only of pressure distribution without also being notified of ski proximity, the skier can generate adequate forward pressure by means of improper ski separation. The applicants have discovered that, since ski proximity is such an important part of proper turn execution as well as in other aspects of skiing, the lack of proximity monitoring results in an incomplete solution to the training challenges surrounding proper ski turns and other aspects of skiing.

Another disadvantage of prior electronic methods is many have not reported changes in pressure against the tongue of a ski boot of each limb independently. They have not associated each sensor with a specific limb, and therefore they have not indicated to the skier which leg was failing to, for example, exceeded a given pressure threshold. Further, the absence of independent, limb-associated sensors has prevented the skier from being able to adjust sensitivity independently for each sensor. This has resulted in an underreported window of improper pressure for one of the two limbs. Prior systems for monitoring skier lean have also typically employed uncomfortable or cumbersome mountings to the ski boot, the ankle, or a combination of the ski boot and ankles. Many of these systems have required semi-permanent to permanent positioning within the ski boot, making maintenance and location adjustment difficult.

BRIEF SUMMARY OF SOME ASPECTS OF DISCLOSURE

The applicants believe that they have discovered at least one or more of the problems and issues with prior art systems noted above as well as advantages variously provided by differing embodiments sports performance monitoring apparatus and methods disclosed in this specification.

In some embodiments, a monitoring system includes pressure sensors respectively adjacent each of a portion of a person's limbs to independently report pressure applied, and/or not applied, to the sensor by the associated limb. In some embodiments, the pressure sensors wirelessly report sensed pressure or absence of pressure to one or more remote reporting device. In some embodiments, sensors can be independently adjusted as desired.

In certain instances, a monitoring system provides a persistent association between a limb and a particular sensor and wirelessly reports information relating to interaction between the sensor and the limb. In some instances, the system provides information allowing the user to learn about that interaction in real time and, if desired, seek to adjust the user's performance in real time as a result.

In certain embodiments, the one or more remote reporting devices can provide an audible sound or other indication in response to information received from one or more sensor. In certain instances, the one or more remote reporting devices provide a left limb audio report to the left ear of the person and a right limb audio monitor report to the right ear of the person.

In some embodiments, at least one sensor includes a bladder, material within the bladder, and a monitor of pressure of the bladder or material in the bladder. In some embodiments, the material within the bladder may be a gel, a fluid, or a mixture of a gel and fluid. In certain embodiments, the fluid may be a liquid; a gas, or a mixture of liquid and gas.

In some instances, at least a portion of the sensor extends adjacent or within a substantial vertical length of a boot. In certain embodiments, the sensor includes a transmitter, and in some embodiments, the transmitter is mountable external of a boot or other footwear. In certain embodiments, the transmitter it mountable to the upper edge of a boot, such as a ski boot in some instances, or other footwear.

In some embodiments, the bladder can extend from a housing containing a transmitter and pressure sensor. In some embodiments, the pressure sensor can monitor pressure or in the bladder and the transmitter can transmit signals based upon or related to the level of pressure sensed by the sensor. As noted above, in certain embodiments, the transmitter can do so wirelessly.

In some instances, the bladder is mountable adjacent the tongue or other portion of a boot, such as a ski boot for example. Pressure in the bladder can increase or decrease in response to pressure applied by a lower leg in the direction of the boot tongue or other portion adjacent to which the bladder is mounted.

In some embodiments, the bladder liner can made of a relatively soft, resilient, elastic, and flexible material. In some embodiments, the bladder liner can include or be made of rubber or synthetic rubber.

In certain instances, the bladder or other sensor can have a relatively long axially extending section, being (i) relatively wide transverse to axis of the axially extending section and (ii) relatively thin transverse to the relatively wide dimension. In some embodiments, the pressure of material within the bladder corresponds to changes in pressure against the bladder and tongue of the boot. This pressure can be sensed by a pressure sensor.

In some embodiments, the bladder can be naturally, conveniently, and/or imperceptibly held in place by friction as a result of the large surface area being in contact with the bladder. In some embodiments, the bladder can allow for a distribution of pressure against and along the surface of the leg within the boot, thus improving comfort and in some instance providing easier long-term use. At least certain embodiments of a bladder can be more economical to implement than one or more piezoelectric or other electronic pressure sensing devices.

In some embodiments, the transmitter is relatively small and has one or more of a generally planar lower side, a curved, arcuate mid-section extending upwardly from the lower side, and a bladder extending from through the lower side of the transmitter body. The curved, arcuate mid-section (or other formation of the transmitter) can include one or more removable battery compartments, batteries, and associated removal structure for gaining access to the one or more battery compartments. At least some of these embodiments can be easily mounted inside a boot, such as a ski boot for example, with the bladder extending within the boot while the transmitter rests on the upper edge of the boot adjacent and somewhat surrounding the user's leg. Some such embodiments can be lightweight as well.

In some embodiments, the bladder can include a bleed valve. In certain embodiments, the bleed valve can enable the material within the bladder, such as gas in some embodiments, to escape when external pressure decreases past a certain point. In some embodiments, the bleed valve can help prevent damage or undesired change in shape of the bladder as the bladder is transported to differing altitudes.

In certain embodiments, the system can include a controller communicable with the transmitter. In some instances, the controller can include a wireless receiver or transceiver. The receiver or transceiver can be adapted to receive transmissions from the transmitter.

In some embodiments, the controller can be relatively small, lightweight, and/or having a curved peripheral shape adapted to be easily grasped by a human hand. Certain instances can be easily handheld and placed in a pocket, such as a jacket or pants pocket for example.

In some embodiments, the system can include headphones or earphones. The headphones or earphones can be adapted to monitor or report sound in response to pressure sensed by the limb pressure sensors. In some embodiments earphones can be very small, lightweight, and/or inexpensive. In other embodiments, the system can include one or more speakers.

In some embodiments, the user can adjust one or more thresholds (pressure levels) detected by the sensor. In some embodiments, a threshold may be set to report pressure going below a predetermined level on or in the sensor. In a skiing application for example, pressure going below this threshold in a boot can cause sound to emit within the associated ear of the person, alerting the person to the situation. The system can be altered to set thresholds as desired and to emit sound, varying sound levels, varying types of sound, or other information (such as pressure level data for example) in the event that, or as, pressure increases or decreases and/or goes above or below one or more thresholds.

In various embodiments, a proximity sensor system can detect distance between limbs, portions of limbs, or associated structure. In some embodiments, the system can determine if such a distance is within, or outside of, a preferred range. In some embodiments, a predetermined proximity range can be adjusted by the user to allow for more precise feedback to assisting the user in correcting the distance between the user's limbs or associated structure.

In some embodiments, the sports performance monitoring apparatus may be used for improvements in skiing technique by detecting pressure applied to the front of each respective ski boot. This allows a skier to know which leg has insufficient forward pressure, enabling the skier to correct pressure application for that leg.

In various embodiments, a proximity sensor can generate real time feedback indicating to the skier that the distance between their skis is inside or outside a preferred range. In some embodiments, a defined proximity range can be adjusted by the skier to allow for more precise feedback to assisting the skier in correcting the distance between their skis.

In some embodiments, one or more proximity sensors and pressure sensors are combined in order to improve the quality and quantity of feedback to the user. In some embodiments, providing an indication that the distance separating the skis are outside of a given range can allow the skier to more easily determine if the skier is correcting pressure distribution by improperly positioning the skier's skis rather than properly redistributing pressure. In addition, through simultaneous monitoring of pressure and proximity the skier can instantly determine if a break in form with respect to desired ski separation correlates to concurrent improper pressure distribution.

In some embodiments, the sports performance monitoring apparatus generates distinctive types of notifications that allow a skier to receive simultaneous feedback for both proximity of skis and skier weight distribution or lean, enabling the skier to make instantaneous adjustments. In some embodiments, the sports performance monitoring apparatus generates distinct audible tones indicating to the skier whether the tone is associated with ski proximity or with pressure distribution, enabling the skier to make the proper type of correction.

In some embodiments, the sports performance monitoring system is lightweight, economical, and/or easy to use and maintain. In certain instances, such a system includes two lightweight sensor units (each having (i) a wireless transmitter housing mountable externally from a boot, and (ii) a pressure sensor with sensing structure (a) extending downwardly form the housing and (b) mountable within a boot), a lightweight controller, and lightweight earbuds connected to the controller. In some embodiments, the controller includes one or more of the following features: (i) adjustable volume controls; (ii) independently adjustable left pressure and right pressure threshold ranges; (iii) independent single-button calibration of left pressure and right pressure reference points; (iv) independent led indicators of active transmission from the left boot sensor unit and the right boot sensor unit; and (v) dual-button switch to calibrate and toggle proximity detection activation.

In some embodiments, the sports performance monitoring system includes two distinct sensor/transmitter components. One of these two components includes a controller, a proximity sensor, a pressure sensor and a transmitter (hereinafter referred to as the "master boot sensor unit"). The other of these two components includes a controller, a pressure sensor and a transmitter (hereinafter referred to as the "secondary boot sensor unit"). In some embodiments, proximity detection is accomplished by the proximity sensor detecting and measuring the strength of the pressure signal transmitted by the secondary boot sensor unit. This has the advantage of reducing the number of sub-components used to detect and report proximity, relying on an unrelated pressure signal and incorporating minimal additional components in the master boot sensor unit, namely, an antenna and receiver.

In some embodiments, the system includes sensor transmission techniques that seek to minimize interference between the system's multiple transmitters. In certain instances, the technique includes unconditional asynchronous transmission by the secondary sensor/transmitter and selective or conditional asynchronous transmission by a master sensor/transmitter that monitors the unconditional asynchronous transmission.

In some methods of sports performance monitoring, the pressure measured by a pressure sensor associated with at least one limb is monitored to provide feedback to a user. In some methods, sensors associated with a left boot pressure and a right boot pressure are monitored to provide more precise feedback to a user to improve sport performance. In some embodiments, a left audio signal is provided based on a monitored left leg pressure and a right audio signal is provided based on a monitored right leg pressure. In some embodiments, proximity between two limbs is also monitored to provide very accurate feedback to a user to quickly improve their skiing ability and technique. Many other novel methods are disclosed herein as well.

There are other novel aspects of the present application. They will become apparent as this specification proceeds. It is therefore to be understood that the scope of the invention is to be determined by the claims as issued and not by whether the claimed subject matter solves any particular problem or all of them, provides any particular features or all of them, or meets any particular objective or group of objectives set forth in the Background or Summary

BRIEF DESCRIPTION OF THE DRAWINGS

The preferred and other embodiments are shown in the accompanying drawings in which.

DETAILED DESCRIPTION OF THE PREFERRED AND OTHER EMBODIMENTS

The following description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, the methods described may be performed in an order different from that described, and various steps may be added, omitted, or combined. Also, features described with respect to certain embodiments may be combined in other embodiments.

Figure 1:
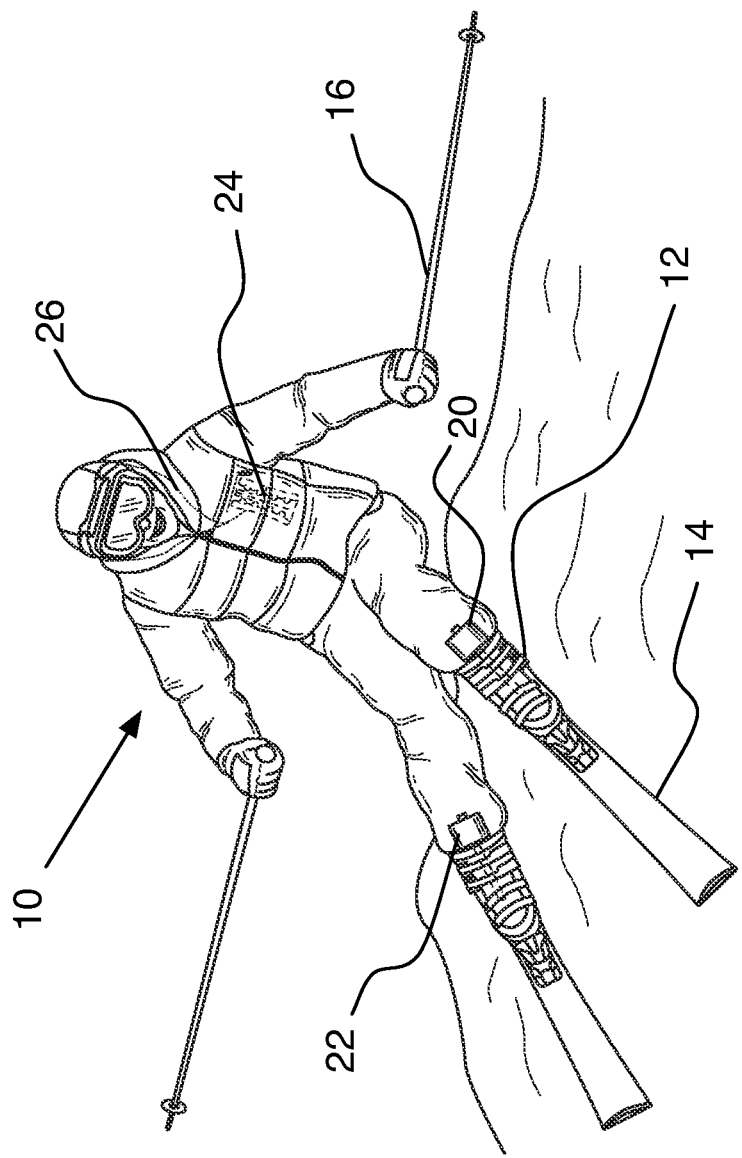
FIG. 1 is a perspective view of a sports monitoring system operated by a skier according to an exemplary embodiment disclosed herein.

With reference to FIG. 1, a skier 10 wearing ski boots 12, which are connected to a pair of skis 14, and holding a pair of ski poles 16 is described. The skier 10 is using an exemplary embodiment of a sports monitoring system, which includes two boot sensor units 20, 22 in communication with a hand controller unit 24. The boot sensor units 20, 22 communicates information regarding the performance of the skier's respective limbs, here the skier's legs, to the skier 10. More particularly, the boot sensor units 20, 22 measures when insufficient pressure, via pressure sensors, is being applied to each respective boot 12 by the skier 10. This information is communicated to the skier 10 via a hand controller unit 24, which may be a wireless controller unit insertable into a pocket of the skier 10. In some embodiments, feedback relating to data received by the hand controller unit 24 from the pressure sensors is communicated to the skier 10 via earphones 26. At least one of the boot sensor units 20, 22 may also contain a proximity sensor, with feedback relating to ski proximity simultaneously communicated to the skier 10 via earphones 26, with the feedback relating to pressure being audibly distinct from feedback relating to proximity.

In alternative embodiments, the hand controller unit 24 may communicate with at least one boot sensor unit 20, 22 through a wire connection. In other embodiments, the boot sensor units 20, 22 may communicate with the hand controller unit 24 via tubes capable of containing a gas, wherein the pressure sensors are air pressure sensors and are located in the hand controller unit 24.

Figure 2:
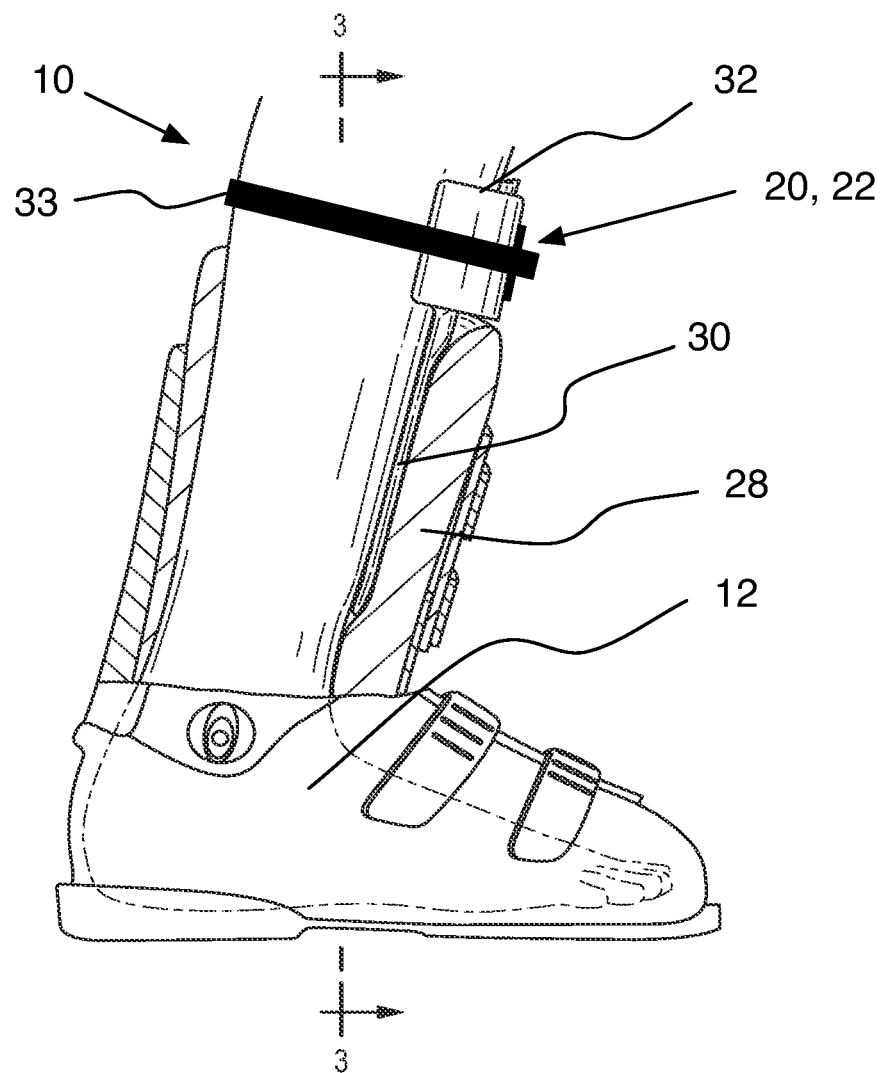
FIG. 2 is a side elevational view of the boot sensor unit of FIG. 1 positioned in a ski boot partially cut out.

With reference to FIG. 2, the boot sensor unit 20, 22 includes a gas-filled bladder 30 made of thin rubber extending from a housing 32, which includes at least a transmitter and a pressure sensor. Each gas-filled bladder is easily insertable between the ski boot 12 and a leg of the skier 10. In the embodiment of FIG. 2, the gas-filled bladder 30 is inserted between the shin of the skier 10 and a tongue 28 of the ski boot 12. The gas-filled bladder 30 is held in place by friction created between the gas-filled bladder 30 and the shin of the skier 10 and between the gas-filled bladder 30 and an inward face of the tongue 28 of the ski boot 12.

The housing 32 is held in place approximately one inch above the top of the tongue 28 of the ski boot 12 by a strap 33. The strap 33 is fastened using Velcro. Alternatively, the bottom side of the housing 32 could rest on the top edge of the boot tongue 28 or other upper boot structure.

The gas-filled bladder 30 is communicatively coupled to at least one pressure sensor that senses pressure of a material contained within the gas-filled bladder 30. The material within the gas-filled bladder 30 may be a gel, a fluid, or a mixture of a gel and fluid. In certain embodiments, the fluid may be a liquid; a gas, or a mixture of liquid and gas. In the embodiment of FIG. 2, the material contained within the gas-filled bladder 30 is ambient air. The pressure of the material within the gas-filled bladder 30 corresponds to changes in pressure against the gas-filled bladder 30 and the tongue 28 of the ski boot 12.

The gas-filled bladder 30 is made of a relatively soft, resilient, elastic, and flexible material. The gas-filled bladder 30 can include or be made of rubber or synthetic rubber. The gas-filled bladder 30 includes a relatively long axially extending section, being relatively wide transverse to axis of the axially extending section and relatively thin transverse to the relatively wide dimension. In the embodiment of FIG. 2, the gas-filled bladder is approximately 8.5 inches long with 0.5 inches of the gas-filled bladder located within the housing 32 to ensure an air-tight seal between the gas-filled bladder 30 and the housing 32. The length of the gas-filled bladder 30 can increase or decrease by anywhere from 10 to 50 percent to better function in different sized boots, ski boots 12, or to provide better sensing, reduce power consumption, etc. In the embodiment of FIG. 2, the gas-filled bladder is approximately 1 inch wide and can theoretically increase to approximately 0.75 inches in depth given full air pressure in the gas-filled bladder 30 to provide accurate pressure sensing without causing discomfort to the skier 10. These dimensions can increase or decrease by anywhere from 10 to 50 percent to better function in different sized boots, ski boots 12, or to provide better sensing, reduce power consumption, etc. It should further be appreciated that the shape of the gas-filled bladder 30 can include various other shapes that, for example, can be inserted between the tongue 28 of the ski boot 12 and the skier 10's leg.

In alternative embodiments, the boot sensor units 20, 22 may include any pressure sensor system that senses pressure along a substantial length of the front of the ski boot 12. These alternative embodiments may include in substitution of or in combination with the gas-filled bladder 30, any of a number of types of pressure sensors placed along a substantial length of the tongue 28 of the ski boot 12 to accurately detect changes in pressure. Any of a number of types of pressure sensors may include, for example compressed gas pressure sensors, piezoresistive strain gauge sensors, capacitive pressure sensors, electromagnetic pressure sensors, piezoelectric pressure sensors, and potentiometric sensors. The specific operation of the pressure sensor(s) will be furthered described in reference to FIG. 8 below. It should also be appreciated that such alternative configurations can be used to detect backward pressure against the ski boot 12, lack of backward pressure against the ski boot 12, or excess pressure against the front of the ski boot 12.

Figure 3:
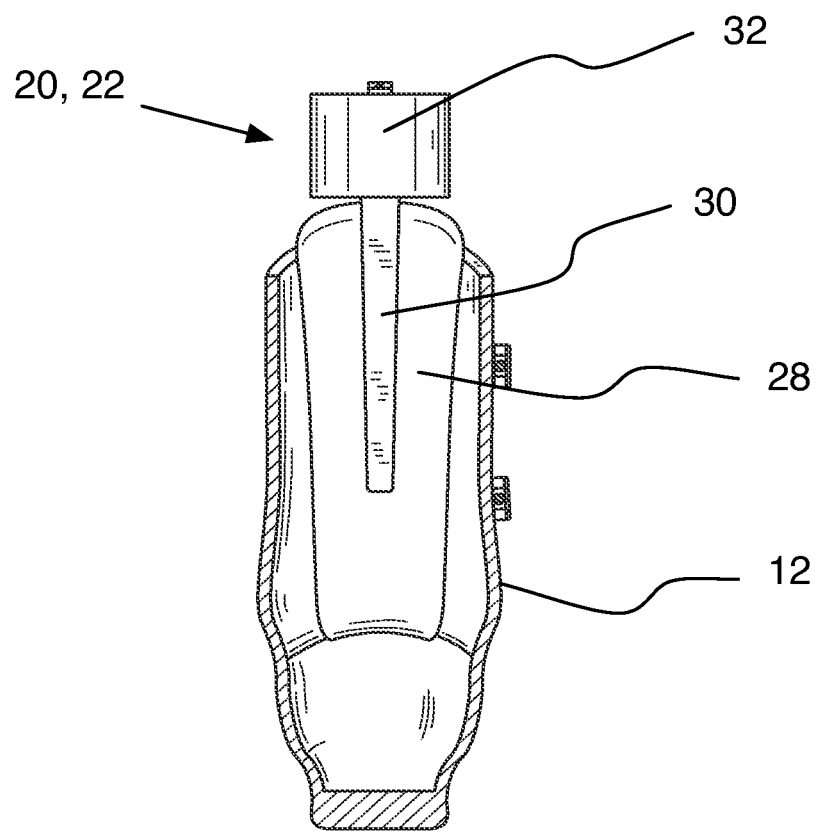
FIG. 3 is a rear cross-sectional view of the boot sensor unit of FIG. 2 mounted adjacent the boot tongue.

With reference to FIG. 3, a more detailed rear view of an exemplary embodiment of the boot sensor unit 20, 22 including a gas-filled bladder 30 extending from the housing 32 is described in contact with the tongue 28 of the ski boot 12. However, it should appreciated that the gas-filled bladder 30 may also be inserted between the leg of the skier 10 and the back of the ski boot 12, or any other position desirable for the improvement of sport performance. For example, in skiing powder conditions, it may be useful for the skier 10 to be notified when insufficient backward pressure is exerted against the ski boot 12 to help the skier 10 keep the skis 14 afloat and prevent the front of the skis 14 from diving into the snow. In this or other circumstances, it may be useful to place the boot sensor unit 20, 22 in the back of the ski boot 12 between the calf of the skier 10 and a back portion of the ski boot 12. Similarly, it may be useful to notify the skier 10 when too much forward pressure is exerted against the tongue 28 of the ski boot 12. This and other such configurations will be further discussed in reference to FIG. 6 below.

Figure 4:
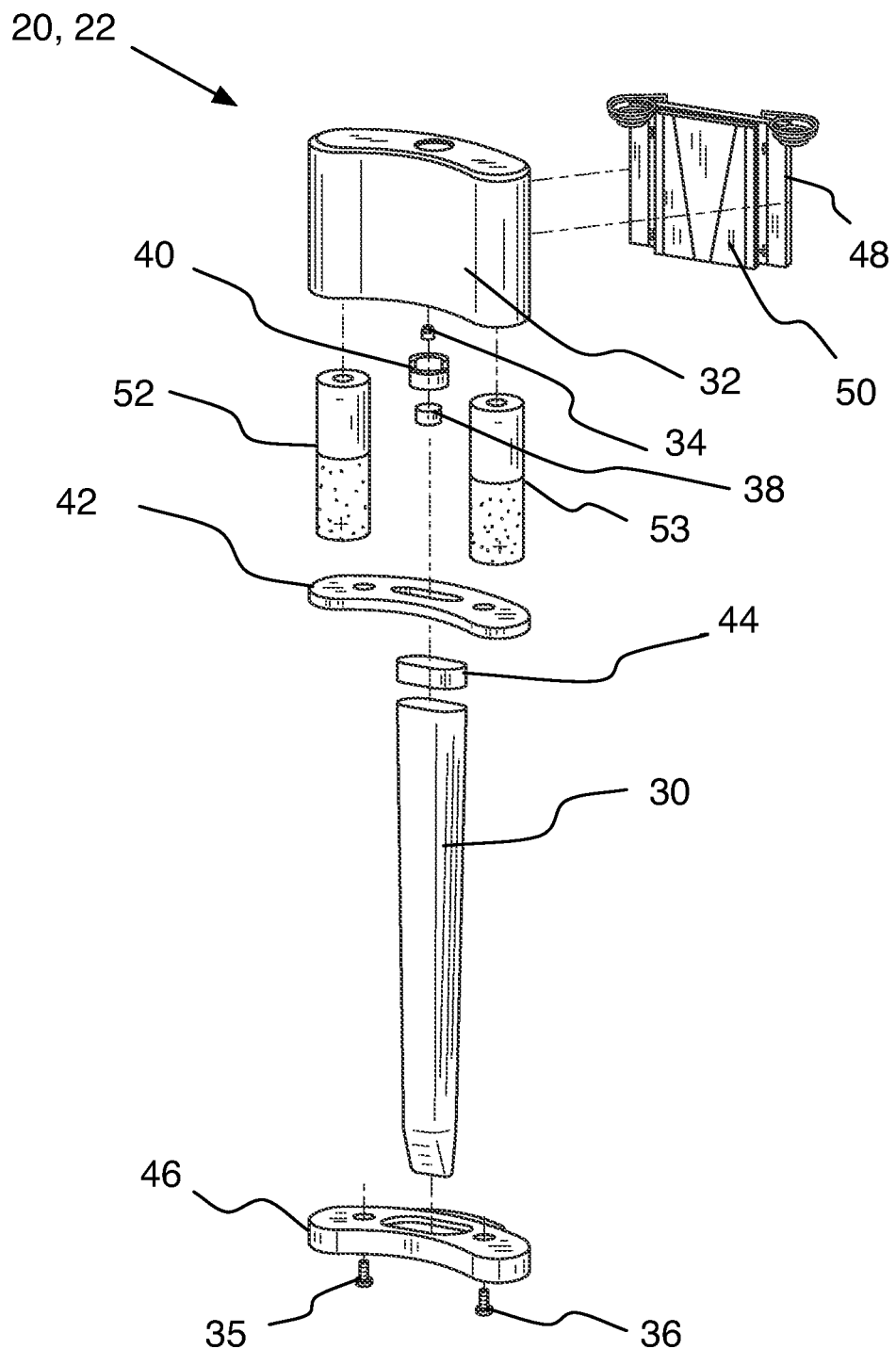
FIG. 4 is an exploded perspective view of the boot sensor unit of FIG. 2.

With reference to FIG. 4, an exploded side view of an exemplary embodiment of the boot sensor unit 20, 22 including the gas-filled bladder 30 extending from the housing 32 is described. The housing 32 is a molded plastic housing. In some embodiments, a button 34, which serves to activate the tact power/reset switch 38, also serves as a bleed valve when located on an upper portion of the housing 32. The purpose of the bleed valve 34 is to allow for pressure normalization at altitude, thus allowing the gas-filled bladder 30 to maintain a normal shape. The tact power/reset switch 38 is protected from unintentional operation by a plastic protective barrier 40. In certain embodiments, the protective barrier 40 is integral to the plastic housing 32. A metal mounting plate 42 connects the housing 32 to a gas-filled bladder plug 44. A cover plate 46, made of bonded rubber, slips over the gas-filled bladder 30 to seal the housing 32 and create an air-tight compartment including a combination of the gas-filled bladder 30 and the housing 32. Fasteners 35, 36 attach the cover plate 46 to the housing 32 to create an air-tight compartment. In the embodiment of FIG. 4, fasteners 35, 36 are threaded screws.

In the embodiment of FIG. 4, the housing 32 has an arcuate shape in the horizontal plane with an interior radius (to be placed in contact with the skier 10's leg) of approximately 1.585 inches and an exterior radius of approximately 0.44 inches. The housing 32 is approximately 2.275 inches tall and approximately 2.879 inches wide and has a depth of approximately 0.726 inches from the interior radius to the exterior radius. Some or all of these dimensions may be increase or decrease anywhere between 10 to 50 percent to reduce weight, to improve sensing, etc. In alternative embodiments, the shape of the housing 32 may also be configured to rest above the back of the ski boot 12 and against the calf of the skier 10.

Also with reference to FIG. 4, two FLASH-based microcontrollers, one including a transmitter 48, and the other including a receiver 50 are described. The transmitter 48 is a UHF ASK/FSK transmitter and the receiver 50 is a UHF ASK/FSK/FM receiver. Both transmitter 48 and receiver 50 are powered by a DC power supply, for example two "AA" alkaline batteries 52, 53. It should be appreciated that various power sources may also be used and may be located separate from the boot sensor unit 20, 22, such as a battery pack wired to the boot sensor unit 20, 22 attachable to a rear of the ski boot 12 or insertable into a pocket of the skier 10. In alternative embodiments, the DC power source may be located external to the boot sensor unit 20, 22 and may wireless communicate with the boot sensor unit 20, 22. The DC power source may be charged via a wireless charging platform. In alternative embodiments, the various components of the boot sensor unit 20, 22 may be consolidated to reduce size and or power consumption of the boot sensor unit 20, 22. The functionality of these components, and various alternative components and schemes to carry out these functionalities, will be further described with reference to FIGS. 5, 8, 9, and 11 below.

In some embodiments, each boot sensor unit 20, 22 weighs approximately 5.7 ounces with the two "AA" alkaline batteries 52, 53 inserted into the housing 32. In some embodiments, the weight of the two boot sensor units 20 and 22 differs based on added functionally included in one or more boot sensor units 20 and 22. For example, one boot sensor unit 20, 22 includes a proximity sensor and weighs approximately 5.9 ounces with the two "AA" alkaline batteries 52, 53 inserted into the housing 32. These weights may increase or decrease from 10 to 50 percent, depending on design. In some embodiments, these weights may decease even further—up to 95 percent may be possible with use of micro- and nanotechnologies.

Figure 5:
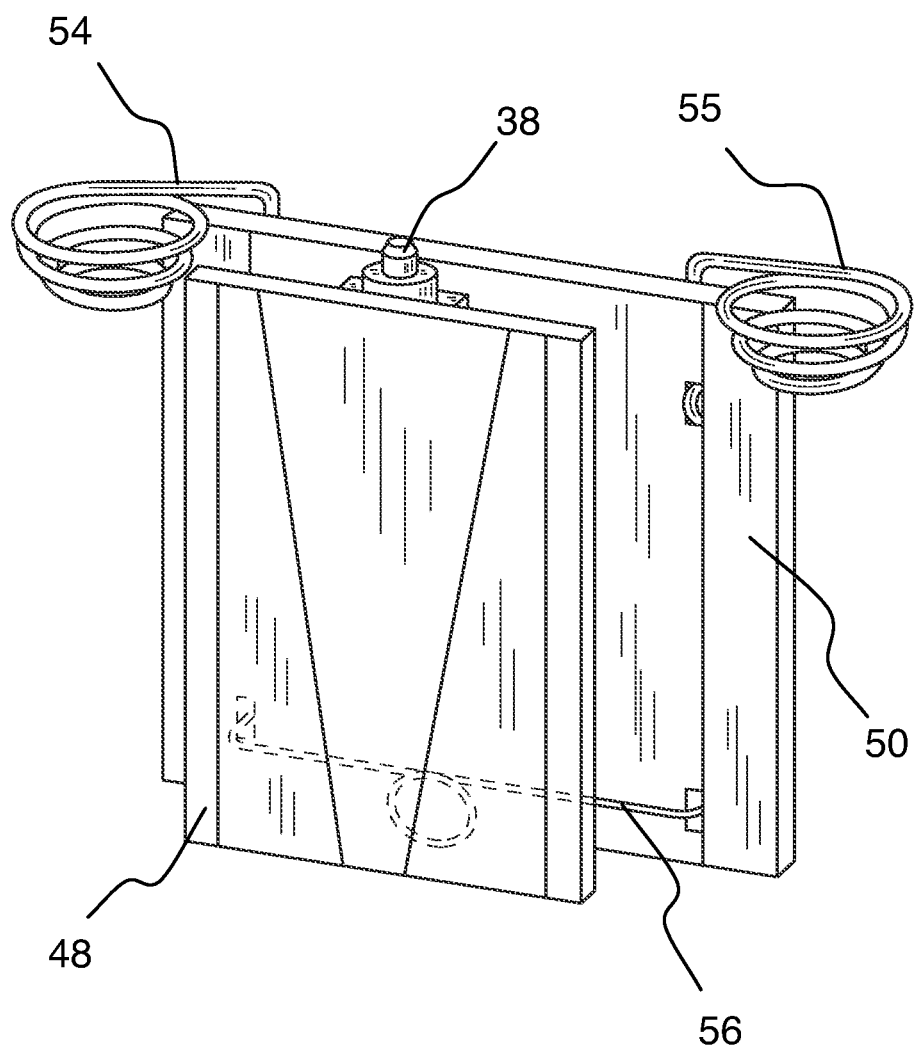
FIG. 5 is a side perspective view showing various components including the transmitter and receiver of the boot sensor unit of FIG. 2.

With reference to FIG. 5, a side perspective view of an exemplary embodiment of negative spring terminals 54, 55, a positive spring terminal 56, and the two microcontroller boards, transmitter 48 and receiver 50 is described. One microcontroller board includes a FLASH-based microcontroller with the UHF ASK/FSK transmitter 48, and the other includes the UHF ASK/FSK/FM receiver 50 as described in reference to FIG. 4. In the embodiment of FIG. 5, the transmitter 48 includes a Microchip® rfPIC12f675 and the receiver 50 includes a Microchip® rfRXD0920, including some or all of the functionality associated therein. The tact power/reset switch 38 is connected to the transmitter 48 and the receiver 50.

In alternative embodiments, the tact power/reset switch 38 may be connected to only one of the transmitter 48 and the receiver 50.

The transmitter 48, the receiver 50 or both may include, for example, a short-range radio frequency (RF) transmitter that sends an RF signal to the hand controller unit 24. It will be readily understood that the transmitter 48 may include any type of wireless transmitter, including, for example, an amplitude modulation (AM) transmitter, a short range digital transmission system such as a Bluetooth® or Zigbee® transmitter, etc. The transmitter 48 may include an RFID tag that communicates with an interrogator located in the hand controller unit 24.

The transmitter 48, the receiver 50, or both may also include various types of intelligent hardware devices, such as a central processing unit (CPU) such as those made by Intel® Corporation or AMD®, a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to allow the boot sensor units 20, 22 to communicate with each other and with the hand controller unit 24. A general-purpose processor may be a microprocessor, but may also be any conventional processor, controller, microcontroller, or state machine. A processor may also be implemented as a combination of computing devices, for example, a combination of a DSP and a microprocessor, multiple microprocessors, one or more microprocessors in conjunction with a DSP core, or any other such configuration.

In alternative embodiments, the transmitter 48, the receiver 50 or both may include one transceiver communicatively coupled to a microcontroller.

Figure 6:
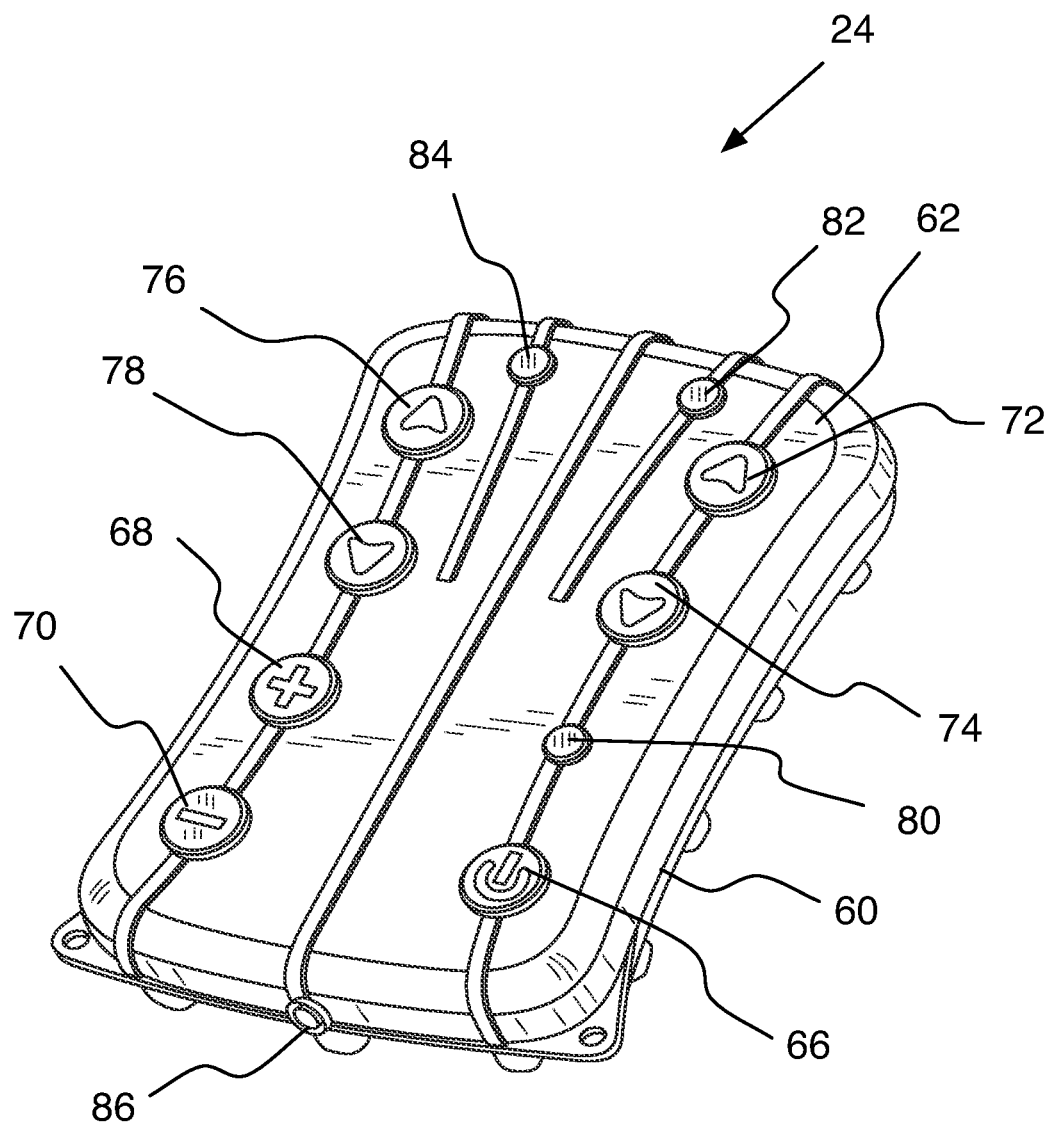
FIG. 6 is a front perspective view of a hand controller unit of the system of FIG. 1.

With reference to FIG. 6, an exemplary embodiment of the hand controller unit 24 that processes various inputs from the boot sensor units 20 and 22 and outputs to the skier 10 is described. The hand controller unit 24 wirelessly communicates with boot sensor units 20 and 22. The hand controller unit 24 includes a hard water resistant plastic housing 60. In some embodiments, a transmitter, a receiver, or both are included within the hard plastic housing 60 of the hand controller unit 24 that allows the hand controller 24 to communicate with at least one of the boot sensor units 20, 22. The hand controller unit 24 includes a DC power source, for example, two "AA" alkaline batteries. It should be appreciated that various power sources may also be used and may be located separate from the hand controller unit 24, such as in a battery pack wired to the hand controller unit 24 and, for example, insertable into a pocket of the skier 10. In alternative embodiments, the DC power source may be located external to the hand controller unit 24 and may wireless communicate with the hand controller unit 24. The DC power source may be charged via a wireless charging platform. In alternative embodiments, the various components described above with reference to the hand controller unit 24 may be consolidated to reduce size and or power consumption of the hand controller unit 24.

There are various buttons protruding through holes in the front cover 62 of the hand controller unit 24 including a power button 66, volume adjust buttons 68, 70, and right and left pressure sensitivity adjustment buttons 72, 74 and 76, 78. The hand controller 24 also includes at least one LED indicator. The various LED indicators include a power indicator LED 80, a right signal receiver indicator LED 82, and a left signal receiver indicator LED 84. When the hand controller unit 24 is powered up via depressing the power button 66, the power indicator LED 80 will blink continually. The LED 80 will blink at one specified rate to indicate satisfactory power is being supplied to the hand controller unit 24, and will blink at a second specified rate to indicate that insufficient power is being supplied to the hand controller unit 24. Such insufficient power may indicate that batteries of the hand controller unit 24 need to be replaced. In the embodiment of FIG. 6, the first specified rate is approximately a one second interval, and the second specified rate is approximately a three second interval.

In alternative embodiments, the skier 10 may be notified of insufficient power being supplied to the hand controller 24 and the boot sensor units 20 and 22 individually via audio signals communicated to the skier 10 via earphones 26.

In the embodiment of FIG. 6, the hand controller unit 24 has a rectangular shape with shorter sides of a convex shape having a radius of approximately 5.816 inches and longer sides of a concave shape having a radius of approximately 9.894 inches. The hand controller unit 24 is approximately 4.952 inches in length, approximately 3.052 inches in width, and approximately 0.695 inches in depth. In alternative embodiments, these dimensions may increase or decrease anywhere between 10 and 50 percent to allow for a more sophisticated user interface, more controls capabilities, etc. In alternative embodiments, the hand controller unit 24 may be contained in a controller attachable to a wrist of the skier 10, attachable to an ear of the skier 10, or in communication with a wireless device of the skier 10, such as a mobile communication device, just to name a few examples.

The hand controller unit 24 weighs approximately 7.2 ounces with two "AA" alkaline batteries inserted into the hard plastic housing 60. This weight may increase or decrease from 10 to 50 percent, depending on design. In some embodiments, this weight may decease even further—up to 95 percent may be possible with use of micro- and nanotechnologies.

When the receiver in the hand controller unit 24 is receiving a signal from at least one boot sensor unit 20, 22 on a paired channel, the corresponding right or left signal receiver indicator LED 82, 84 will blink continually. This informs the skier 10 that the system is sending and receiving signals. In alternative embodiments, in response to receiving a signal from at least one boot sensor unit 20, 22, the hand controller unit 24 generates an audio output signal and sends this audio signal to a 3.5 mm stereo audio jack 86.

The LED 82, 84 will blink at one specified rate to indicate satisfactory power is being supplied to each of the boot sensor units 20, 22 and will blink at a second specified rate to indicate that insufficient power is being supplied to each of the boot sensor units 20, 22. Such insufficient power may indicate that batteries 52, 53 of the respective boot sensor units 20, 22 need to be replaced. In the embodiment of FIG. 6, the first specified rate is a one second interval, and the second specified rate is a three second interval.

The power button 66 will power up the system if depressed for two seconds. In some embodiments, the power button 66 will further silence tone generation if depressed for two seconds, reactivate inactive boot sensor units 20, 22 if depressed for two seconds, and power down the sports monitoring system if depressed for five seconds. In alternative embodiments, these time periods and button functions may be varied.

The volume adjustment buttons 68, 70 increase or decrease the volume of a tone output to the stereo audio jack 86 one step for each time either button is depressed. When depressed, a tone will be generated and output to the stereo audio jack 86 allowing the skier 10 to select a desired level. A right sensitivity and a left sensitivity are set by depressing and holding each of the right sensitivity adjustment button 74 and the left sensitivity adjustment button 78 simultaneously for a set period of time. In the embodiment of FIG. 6, the set period of time is approximately three seconds. A right forward pressure point and a left forward pressure point will be set upon depressing the right sensitivity adjustment button 74 and the left sensitivity adjustment button 78 for approximately three seconds, at which time a tone is generated in each earphone 26 to indicate to the skier 10 that the pressure thresholds have been set. The right sensitivity adjustment buttons 72, 74 and the left sensitivity adjustment buttons 76, 78 control the sensitivity of the pressure sensor by adjusting a threshold value that is compared to the pressure data received from the boot sensor units 20, 22. The signal from each of the boot sensor units 20, 22 is converted to a value that is then be compared to the corresponding right or left threshold setting. If the value is below the threshold setting, a tone is generated on the corresponding channel of the stereo output jack 86.

In alternative embodiments, the hand controller unit 24 may further include a tone inversion switch that toggles the audio output between two states. The default setting generates a tone when there is a state of no forward pressure against a gas-filled bladder 30 as compared to the threshold pressure value. The reverse setting may generate a tone when there is sufficient forward pressure against a gas-filled bladder 30 as compared to the threshold pressure value. This reverse setting may be useful, for example, when the skier 10 is skiing in powder conditions and too much forward pressure against the boots 12 may cause the skis 14 to dive into the snow and inhibit performance. Further, this reverse setting may also be useful, for example, for bump skiing where too much forward pressure may case less than optimal performance. It should be appreciated that this reverse setting may be useful in other ski conditions and circumstances. It should also be appreciated that this reverse setting may be used in combination with a placement of the boot sensor units 20, 22 in the back of the ski boot 12 to indicate inadequate forward pressure, similar to the default setting when the boot sensor unit 20, 22 is placed in the front of the ski boot 12.

The left sensitivity adjustment button 78 and the right sensitivity adjustment button 74 toggle activation of proximity monitoring if depressed simultaneously for a set period of time. In the embodiment of FIG. 6, the set period of time is approximately two seconds.

In alternative embodiments, different combinations of buttons held for various time periods may also be used for the various functionalities described above.

Figure 7:
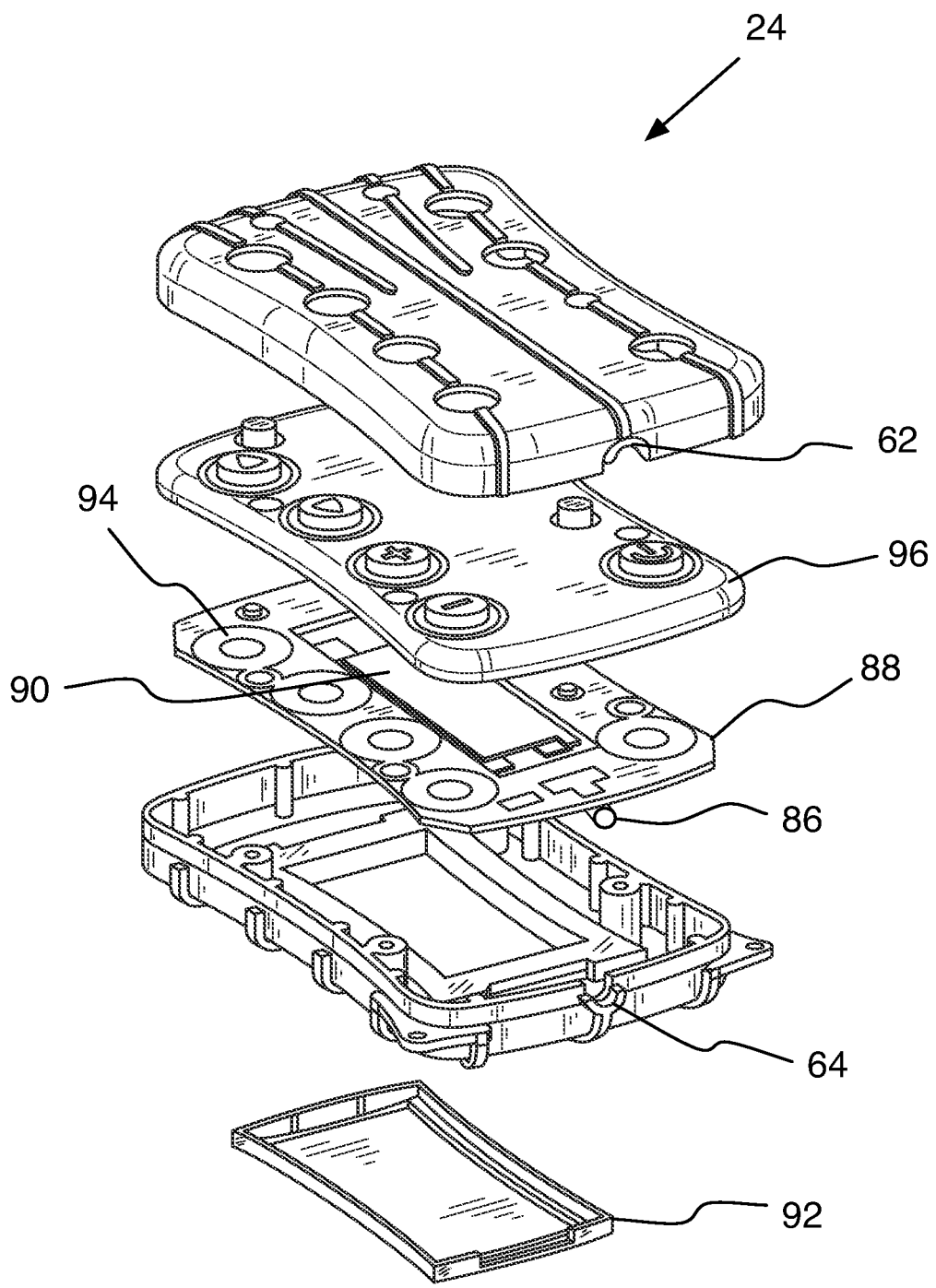
FIG. 7 is an exploded perspective view of the hand controller unit illustrated in FIG. 6.

With reference to FIG. 7, an exploded front angle view of an exemplary embodiment of the hand controller unit 24 is described. The 3.5 mm stereo audio jack 86 is attached to the back of a printed circuit board 88 flush with the lower edge. A microcontroller 90 is located on the printed circuit board 88. The hard plastic housing 60 further includes a front cover 62 and a back cover 64. Cutouts in the front cover 62 and the back cover 64 allow for access to the stereo audio jack 86 for the earphones 26. A removable battery cover 92 that snaps into a locking position to cover a cutout in the back cover 64 allows for access to a power source, which consists of two "AA" alkaline batteries positioned on a surface of the printed circuit board 88. It should be appreciated that other power sources may be used. Switch pads 94 are located on the printed circuit board 88 that correspond to the buttons on a contact-sensitive silicone rubber keypad 96.

The microcontroller 90 includes a FLASH-based microcontroller with a UHF ASK/FSK receiver, such as a Microchip® rfRXD0920. In the embodiment of FIG. 7, the microcontroller 90 further includes a Microchip® rfPIC12F675 controller in communication with the UHF ASK/FSK receiver Microchip® rfRXD0920. The functionality and components of the controller 90 will be further described with reference to FIG. 10 below.

Figure 8:
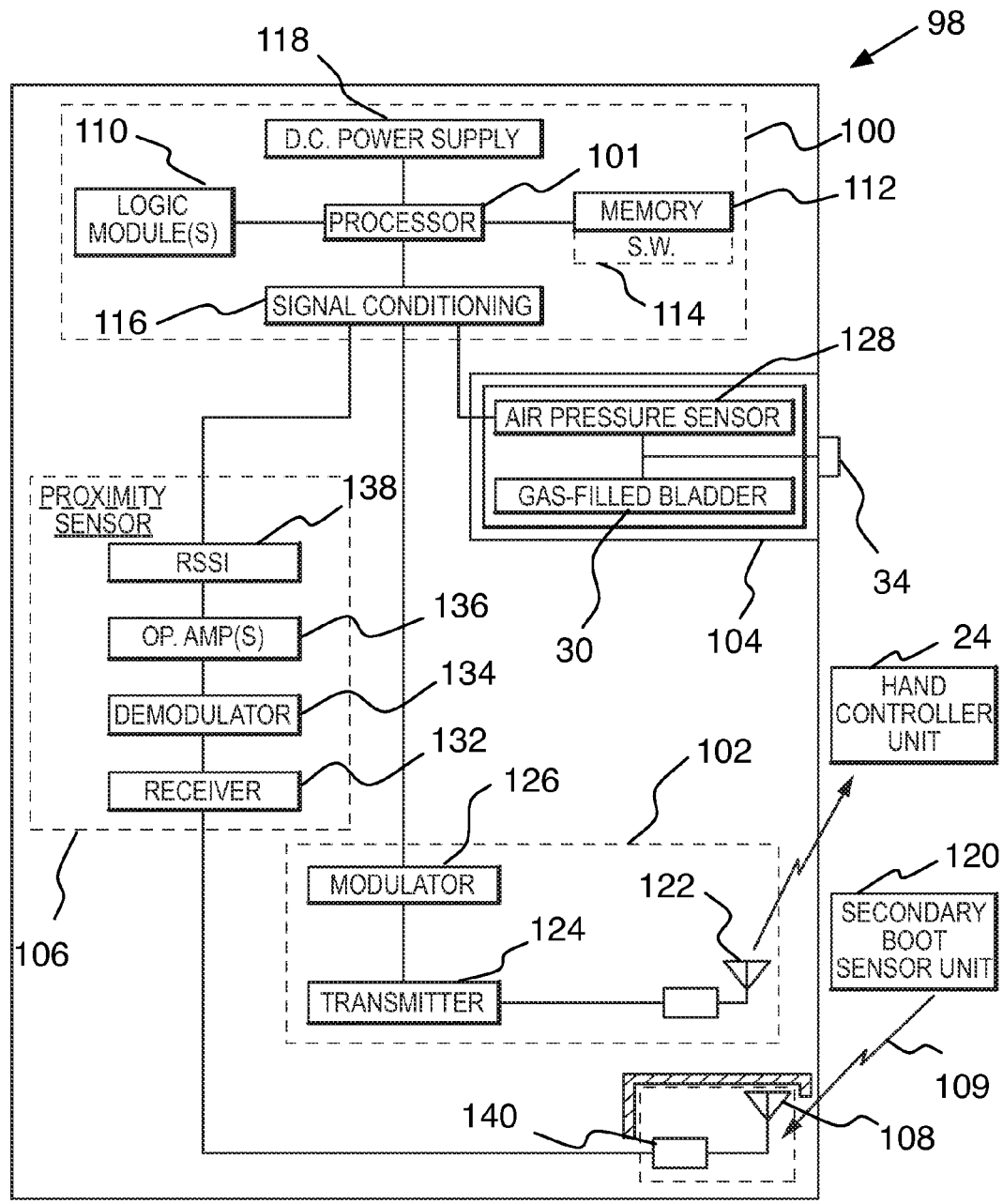
FIG. 8 is a schematic diagram of components associated with a master boot sensor unit of FIG. 2.

With reference now to FIG. 8, a block diagram of components associated with a master boot sensor unit 98, which can be one of the boot sensor units 20, 22, according to an exemplary embodiment is disclosed herein. The master boot sensor unit 98 is illustrated for purposes of discussion, with the understanding that other boot sensor units may include the same or similar components, functionality, or both of the master boot sensor unit 98. In the embodiment of FIG. 8, the master boot sensor unit 98 includes a control module 100, a transmitter unit 102 communicatively coupled to the control module 100 for communicating sensor data to the hand controller unit 24, a pressure sensor unit 104 communicatively coupled to the control module 100, and a proximity sensor unit 106 communicatively coupled to both the control module 100 and at least one proximity antenna 108. It should be understood that all of the above-stated components may be implemented on transmitter 48, receiver 50 or both as described in reference to FIGS. 4 and 5 above.

The control module 100 includes a processor 101, one or more logic modules 110, a memory 112 that contains software 114 for execution by one or more logic modules 110, and signal conditioning 116, which is configured to convert signals from analogue to digital or digital to analogue formats. The control module 102 further includes a D.C. power supply 118, for example, two "AA" alkaline batteries 52, 53.

The logic module(s) 110, the memory 112, and the processor 101 may be implemented using one or more intelligent hardware devices, as referenced above, such as a central processing unit (CPU) such as those made by Intel® Corporation or AMD®, a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to allow the master boot sensor unit 98 to communicate with a secondary boot sensor unit 120 and with the hand controller unit 24. A general-purpose processor may be a microprocessor, but may also be any conventional processor, controller, microcontroller, or state machine. A processor may also be implemented as a combination of computing devices, for example, a combination of a DSP and a microprocessor, multiple microprocessors, one or more microprocessors in conjunction with a DSP core, or any other such configuration.

The memory 112 may include random access memory (RAM), read-only memory (ROM), EEPROM, CD-ROM or other optical disk storage, magnetic disk storage or other magnetic storage devices, any combination thereof, or any other medium that can be used to carry or store desired program code in the form of instructions or data structures and that can be accessed by a general-purpose or special-purpose processor or computer. The memory 112 may store computer-readable, computer-executable software code 114 containing instructions that are configured to, when executed (or when compiled and executed), cause the logic modules 110, the processor 101, or both to perform various functions described herein (e.g., pressure detection, proximity detection, transmission and reception of one or more signals using a one or more communication channels, etc.).

The components of the control module 100 may, individually or collectively, be implemented with one or more Application Specific Integrated Circuits (ASICs) adapted to perform some or all of the applicable functions in hardware. The control module 100 may also include any intelligent hardware device as described above. In the embodiment of FIG. 8, the control module 100 is implemented using a high-performance, 16-bit digital signal controller, such as a Microchip® dsPIC33FJ64MCX02, which performs some or all of the functionalities described above.

The transmitter unit 102, which may be the transmitter 48 as shown in FIGS. 4 and 5, includes one or more antennas 122 communicatively coupled with one or more transmitters 124 for transmitting sensor data to the hand controller unit 24. The transmitter unit 102 further includes a modulator 126 that is communicatively coupled with both the transmitter 124 and the control module 100 to further effectuate quality robust transmission by modulating the sensor data communicated to the hand controller 24.

The transmitter unit 102 includes, as described above, for example, a short range radio frequency (RF) transmitter that sends an RF signal to the hand controller unit 24. In alternative embodiments, the transmitter unit 102 may be a FLASH-based microcontroller with a UHF ASK/FSK transmitter. It will be readily understood that the transmitter may include any type of wireless transmitter, including, for example, an amplitude modulation (AM) transmitter, a short range digital transmission system such as a Bluetooth® or Zigbee® transmitter, etc. In the embodiment of FIG. 8, the transmitter unit 102 is a Microchip® rfPIC12F675H, utilizing some or all of the functionalities associated therein.

The transmitter unit 102 includes an RFID tag that communicates with an interrogator located in the hand controller unit 24. For example, the transmitter unit 102 may transmit, via one or more antennas 122, a relatively low-power frequency modulated (FM) signal that includes a left and a right channel to the hand controller unit 24. When a signal is received by the control module 100 from the pressure sensor unit 104, a first signal is generated that is modulated onto the left channel of the FM signal, which is received at the hand controller unit 24, demodulated, and provided as a tone to the skier 10 via a left earphone 26. When the skier 10 hears the tone in their left ear, it indicates that an incorrect amount of pressure is being applied to the master boot sensor unit 98. Similarly, if the proximity sensor unit 106 generates an output indicating the proximity of one or more sensors is outside of a predetermined proximity range, the control module 100 of the master boot sensor unit 98 receives a signal from the proximity sensor unit 106 and generates a second signal that is modulated onto both a left channel and right channel of the FM signal. When the FM signal is received at the hand controller unit 24, a second tone is demodulated and provided to the skier 10 via left and right earphones 26. When the skier 10 hears the tone in both ears, it indicates that the master boot sensor unit 98 is either too close or too far away from one or more other boot sensors units 20, 22, which may include the secondary boot sensor unit 120.

The antenna 122 is a monopole antenna. The antenna 122 includes a copper strip with a length corresponding to a fractional value of a desired frequency of the sports monitoring system. In the embodiment of FIG. 8, the antenna 122 is one half a wavelength of the operating frequency of the sports monitoring system. The sports monitoring system operates at a frequency of 904 MHz. One skilled in the art will readily recognize that other antenna designs, other operating frequencies, and/or systems may implement the functionality of the antenna 122, and that such antennas can be implemented as embedded components on printed circuit boards.

The pressure sensor unit 104 includes an air pressure sensor 128, the gas-filled bladder 30, and the bleed valve 34. The pressure sensor unit 104 may also include any of a number of types of pressure sensors, for example compressed gas pressure sensors, piezoresistive strain gauge sensors, capacitive pressure sensors, electromagnetic pressure sensors, piezoelectric pressure sensors, and potentiometric sensors. The air pressure sensor 128 includes a miniaturized Manifold Absolute Air Pressure sensor, such as an Infineon® TurboMap® or Infineon® KP229E3518. The air pressure sensor 128 continuously communicates a pressure value to the control module 100. In alternative embodiments, the air pressure sensor 128 may periodically communicate a pressure value to the control module 100. The signal conditioning 116 receives the pressure value communicated from the air pressure sensor 128 and performs various filtering and modification of the pressure value before communicating the pressure value to the processor 101.

The air pressure sensor 128, the gas filled bladder 30, and the bleed valve 34 make up a sealed air-tight system. The gas-filled bladder 30 may be constructed of a soft, elastic synthetic rubber, or any other similar material. The bleed valve 34 is combined with the tact power/reset switch 38 to form a single switch. In alternative embodiments, the bleed valve 34 may be independent of tact power/reset switch 38.

The proximity sensor unit 106 includes a receiver 132, a demodulator 134, operational amplifier(s) 136, and a Received Signal Strength Indicator (RSSI) 138. The receiver 132 receives and processes a signal from a proximity antenna 108. The demodulator 134 then recovers the information content from the modulated signal received by the proximity antenna 108 and sent to the receiver 132. The RSSI 138 then extracts the desired received signal strength in order to communicate that information to the signal conditioning 116. The signal conditioning 116 in conjunction with the processor 101, the logic module(s) 110, the memory 122, and the software 114 then process the received signal strength in order to transmit a signal to the hand controller unit 24 indicative of proximity via the transmitter unit 102.

The receiver 132 is communicatively coupled to the proximity antenna 108, which is configured to receive a signal indicative of proximity. The proximity sensor unit 106 detects proximity based on a magnitude of the strength of a signal received by the proximity antenna 108 via the RSSI 138. A signal is received from the secondary boot sensor unit 120. In the embodiment of FIG. 8, the signal is a pressure sensor signal sent by the secondary boot sensor unit 120. In alternative embodiments, the signal may be a proximity specific signal transmitted by the secondary boot sensor unit 120.

In the embodiment of FIG. 8, the proximity antenna 108 is a U-shaped monopole antenna partially shielded by a metallic shield 140. The metallic shield includes a non-metallic substrate in contact with a metallic layer, positioned with the metallic layer facing away from the proximity antenna 108. In some embodiments, the metallic layer may include aluminum or copper.

The proximity sensor unit 106 may be any of a number of types of proximity sensors, including inductive, magnetic, or RF-based proximity sensors. In the embodiment of FIG. 8, the proximity sensor unit 106 includes a FLASH-based microcontroller with a UHF ASK/FSK receiver, such as a Microchip® rfRXD0920.

Figure 9:
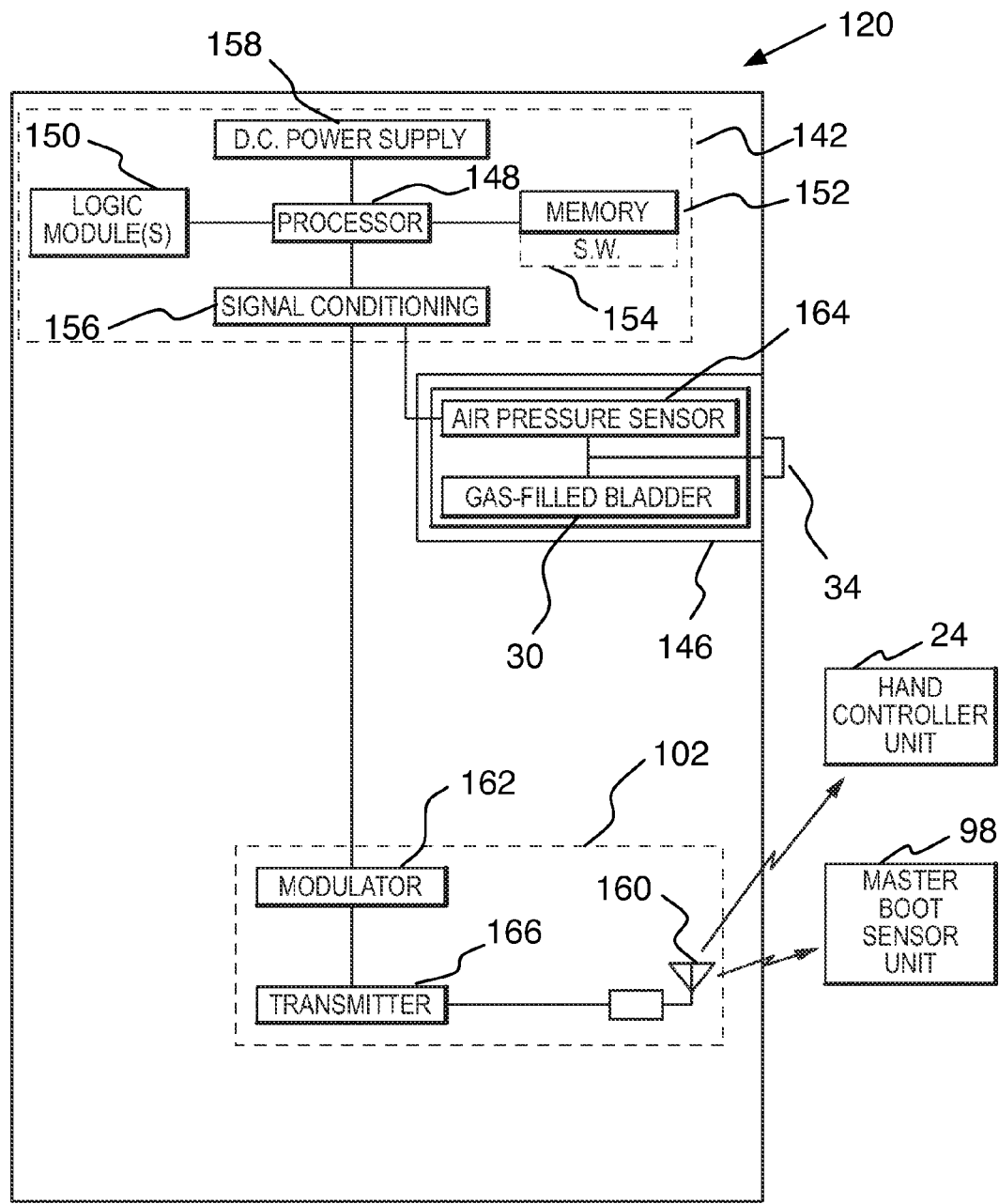
FIG. 9 is a schematic diagram of components of the secondary boot transmitter unit of FIG. 2.

With reference now to FIG. 9, a block diagram of components associated with the secondary boot sensor unit 120, which may be one of the boot sensor units 20, 22, according to an exemplary embodiment is described. The secondary boot sensor unit 120 is illustrated for purposes of discussion, with the understanding that the secondary boot sensor unit 120 (or other boot sensor units) may include the same or similar components, functionality, or both as that of the master boot sensor unit 98. It should be appreciated that many of the components implemented in the master boot sensor unit 98 may also be implemented in the secondary boot sensor unit 120 for simplicity and ease of use and maintenance. It should also be appreciated that the components of the secondary boot sensor unit 120 may be partially or completely different from those described with reference to FIG. 8.

The secondary boot transmitter 120 includes a control module 142 and a transmitting unit 144 and a pressure sensor unit 146 each communicatively coupled to the control module 142. The control module 142 includes a processor 148, one or more logic modules 150, a memory 152 that contains a software 154 for execution by one or more logic modules 150, and a signal conditioning 156, which is configured to convert signals from analogue to digital or digital to analogue formats. The control module 142 further includes a D.C. power supply 158, for example, two "AA" alkaline batteries 52, 53. It should be understood that some or all of the above components may be implemented on transmitter 48.

The logic module(s) 150, the memory 152, and the processor 148 may be implemented using one or more intelligent hardware devices, as referenced above, such as a central processing unit (CPU) such as those made by Intel® Corporation or AMD®, a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to allow the secondary boot sensor unit 120 to communicate with the master boot sensor unit 98 and with the hand controller unit 24. A general-purpose processor may be a microprocessor, but may also be any conventional processor, controller, microcontroller, or state machine. A processor may also be implemented as a combination of computing devices, for example, a combination of a DSP and a microprocessor, multiple microprocessors, one or more microprocessors in conjunction with a DSP core, or any other such configuration.

The memory 152 may include random access memory (RAM), read-only memory (ROM), EEPROM, CD-ROM or other optical disk storage, magnetic disk storage or other magnetic storage devices, any combination thereof, or any other medium that can be used to carry or store desired program code in the form of instructions or data structures and that can be accessed by a general-purpose or special-purpose processor or computer. The memory 152 stores computer-readable, computer-executable software code 154 containing instructions that are configured to, when executed (or when compiled and executed), cause the logic module 150, the processor 148, or both to perform various functions described herein (e.g., pressure detection, transmission of one or more signals using a one or more communication channels, etc.).

The components of the control module 142 may, individually or collectively, be implemented with one or more Application Specific Integrated Circuits (ASICs) adapted to perform some or all of the applicable functions in hardware. The control module 142 may also include any intelligent hardware device as described above. In the embodiment of FIG. 9, the control module 142 is implemented using a high-performance, 16-bit digital signal controller, such as a Microchip® dsPIC33FJ64MCX02, which performs some or all of the functionalities described above.

The transmitter unit 144, which may be the transmitter 48 as described with reference to FIGS. 4 and 5, includes one or more antennas 160 communicatively coupled with one or more transmitters 166 for transmitting sensor data to the hand controller unit 24 and the master boot sensor unit 98. The transmitter unit 144 further includes a modulator 162 that is in communicatively coupled with both the transmitter 146 and the control module 142 to further effectuate quality robust transmission to the hand controller unit 24 and the master boot sensor unit 98.

The transmitter unit 144 includes, as described above, for example, a short range radio frequency (RF) transmitter that sends an RF signal to the hand controller unit 24. In alternative embodiments, the transmitter unit 144 may be a FLASH-based microcontroller with a UHF ASK/FSK transmitter. It will be readily understood that the transmitter may include any type of wireless transmitter, including, for example, an amplitude modulation (AM) transmitter, a short range digital transmission system such as a Bluetooth® or Zigbee® transmitter, etc. In the embodiment of FIG. 9, the transmitter unit 144 is a Microchip® rfPIC12F675H. It should also be appreciated that the functions performed by the control module 142 may also be partially or fully performed by the transmitter unit 144 including a Microchip® rfPIC12F675H.

In the embodiment of FIG. 9, transmitter unit 144 also sends an RF signal to the master boot sensor unit 98 to facilitate detection of proximity by the master boot sensor unit 98.

The transmitter unit 144 includes an RFID tag that communicates with an interrogator located in the hand controller unit 24. For example, the transmitter unit 144 may transmit, via one or more antennas 160, a relatively low-power frequency modulated (FM) signal that includes a left and a right channel to the hand controller unit 24. When a signal is received by the control module 142 from the pressure sensor unit 146, a first signal is generated that is modulated onto a right channel of the FM signal, which is received at the hand controller unit 24, demodulated, and provided as a tone to the skier 10 via a right earphone 26. When the skier 10 hears the tone in their right ear, it indicates that an incorrect amount of pressure is being applied to the secondary boot sensor unit 120.

The antenna 160 is a monopole antenna. The antenna 160 includes a copper strip with a length corresponding to a fractional value of a desired frequency of the sports monitoring system. In the embodiment of FIG. 9, antenna 160 is one half a wavelength of the operating frequency of the sports monitoring system. The sports monitoring system operates at a frequency of 904 MHz. One skilled in the art will readily recognize that other antenna designs, other operating frequencies, and/or systems may implement the functionality of the antenna 160.

The pressure sensor unit 146 includes an air pressure sensor 164, the gas-filled bladder 30, and the bleed valve 34. The pressure sensor unit 164 may also include any of a number of types of pressure sensors, for example compressed gas pressure sensors, piezoresistive strain gauge sensors, capacitive pressure sensors, electromagnetic pressure sensors, piezoelectric pressure sensors, and potentiometric sensors. In the embodiment of FIG. 9, the air pressure sensor 164 includes a miniaturized Manifold Absolute Air Pressure sensor, such as an Infineon® TurboMap® or Infineon® KP229E3518. The air pressure sensor 164 continuously communicates a pressure value to the control module 142. In alternate embodiments, the air pressure sensor 164 may periodically communicate a pressure value to the control module 142. The signal conditioning 156 receives the pressure value communicated from the air pressure sensor 164 and performs various filtering and modification of the pressure value before communicating the pressure value to the processor 148.

The air pressure sensor 164, the gas filled bladder 30, and the bleed valve 34 make up a sealed air-tight system. The gas-filled bladder 30 may be constructed of a soft, elastic synthetic rubber, or any other similar material. The bleed valve 34 is combined with the tact power/reset switch 38 to form a single switch. In alternative embodiments, the bleed valve 34 may be independent of the tact power/reset switch 38.

With this basic structure in mind, it should be appreciated that the above components may operate and be arranged, with all alternative embodiments, as is described above with respect to the master boot sensor unit 98 as shown in FIG. 8. However, in some embodiments, the secondary boot sensor unit 120 does not contain a proximity sensor unit 106 or a proximity antenna 108. In the embodiment of FIG. 9, the secondary boot sensor unit 120 is configured to communicate pressure sensor information in all directions. The master boot sensor unit 98 is configured to receive the pressure sensor information communicated by the secondary boot sensor unit 120 via the proximity antenna 108 and to determine proximity of the secondary boot sensor unit 120 with respect to the master boot sensor unit 98.

Figure 10:
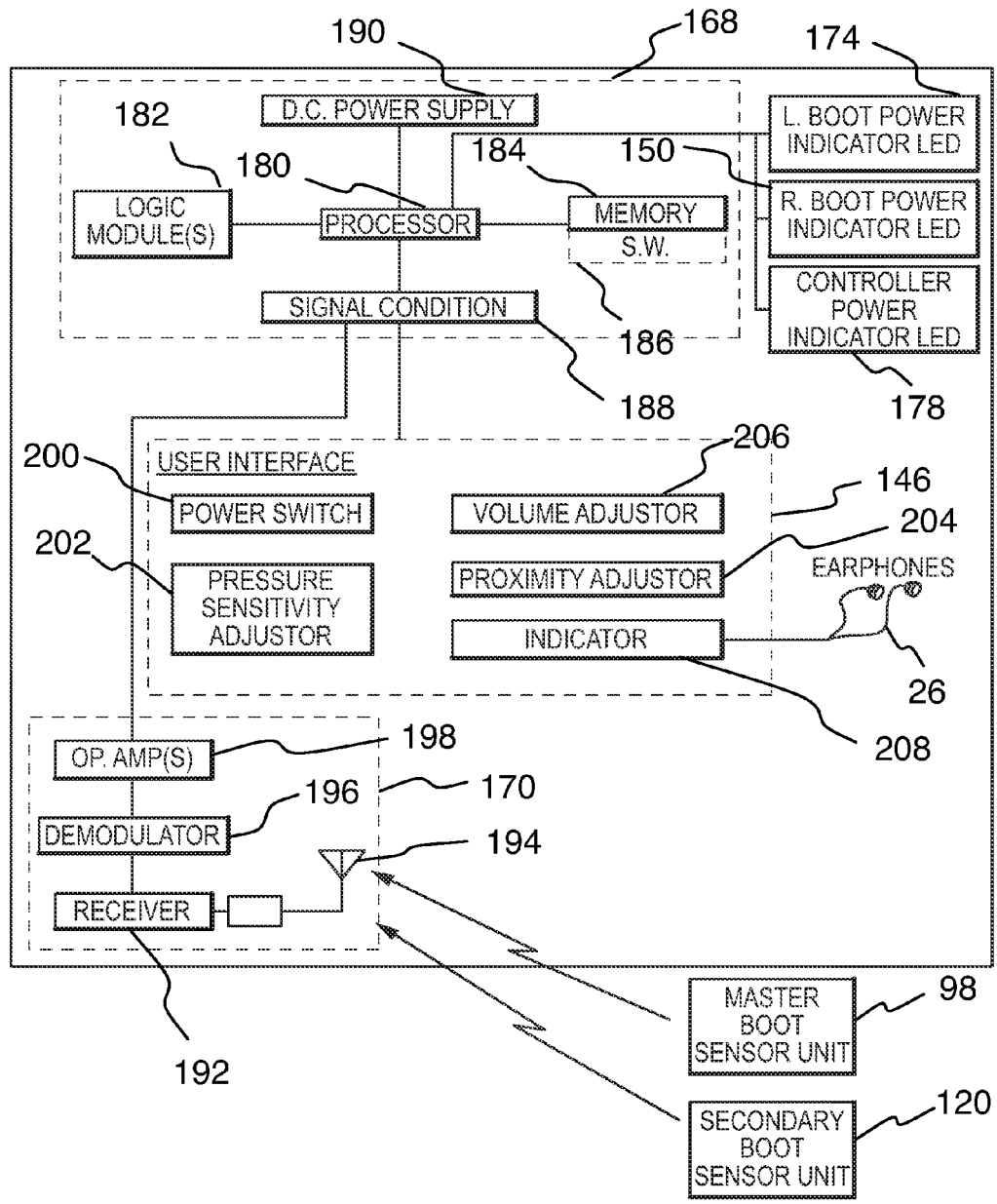
FIG. 10 is a schematic diagram of the components of the hand controller unit of FIGS. 6-7.

With reference now to FIG. 10, a block diagram of components associated with the hand controller unit 24 according to an exemplary embodiment is described. The hand controller unit 24 is in communication with the master boot sensor unit 98 and the secondary boot sensor unit 120. The hand controller unit 24 includes a control module 168, which may include some or all of the functionality and components of the control module 100 associated with the master boot sensor unit 98 or the control module 142 associated with secondary boot sensor unit 120. The control module 168 is commutatively coupled to a receiver unit 170 and a user interface 172.

The control module 168 further includes a processor 180, one or more logic modules 182, a memory 184 that contains a software 186 for execution by one or more logic modules 182, and a signal condition 188, which is configured to convert signals from analogue to digital or digital to analogue formats. The control module 168 further includes a D.C. power supply 190, for example, two "AA" alkaline batteries.

The logic modules 182 and the memory 184 may be implemented using one or more intelligent hardware devices, as similarly described above, such as a central processing unit (CPU) such as those made by Intel® Corporation or AMD®, a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to allow the hand controller unit 24 to communicate with the master boot sensor unit 98 and the secondary boot sensor unit 120. A general-purpose processor may be a microprocessor, but may also be any conventional processor, controller, microcontroller, or state machine. A processor may also be implemented as a combination of computing devices, for example, a combination of a DSP and a microprocessor, multiple microprocessors, one or more microprocessors in conjunction with a DSP core, or any other such configuration.

The memory 184 may include random access memory (RAM), read-only memory (ROM), EEPROM, CD-ROM or other optical disk storage, magnetic disk storage or other magnetic storage devices, any combination thereof, or any other medium that can be used to carry or store desired program code in the form of instructions or data structures and that can be accessed by a general-purpose or special-purpose processor or computer. The memory 184 stores computer-readable, computer-executable software code 186 containing instructions that are configured to, when executed (or when compiled and executed), cause the logic module 182 or the control module 182 to perform various functions described herein (e.g., reception of one or more signals using a left and/or right communication channel, signal processing, user indication, etc.).

The components of the control module 168 may, individually or collectively, be implemented with one or more Application Specific Integrated Circuits (ASICs) adapted to perform some or all of the applicable functions in hardware. In some embodiments, the control module 168 may also include any intelligent hardware device as described above. In the embodiment of FIG. 10, the control module 168 is implemented using a high-performance, 16-bit digital signal controller, such as a Microchip® rfPIC12F675.

The control module 168 is communicatively coupled to at least one power indicator. In the embodiment of FIG. 10, the various power indicators include a left boot power indicator LED 174, a right boot power indicator LED 176, and a controller power indicator LED 178. The left boot power indicator LED 174, the right boot power indicator LED 176, and the controller power indicator LED 178 correspond to the left signal receiver indicator LED 84, the right signal receiver indicator LED 82, and the power indicator LED 80. When the hand controller unit 24 is powered up, the controller power indicator LED 178 will blink continually. The LED 178 will blink at one specified rate to indicate satisfactory power is being supplied to hand controller unit 24, and will blink at a second specified rate to indicate that insufficient power is being supplied to the hand controller unit 24. Such insufficient power may indicate that the DC power supply 190 of the hand controller unit 24 needs to be replaced. In the embodiment of FIG. 10, the first specified rate is approximately a one second interval, and the second specified rate is approximately a three second interval.

When the receiver unit 170 in the hand controller unit 24 is receiving a signal from the master boot sensor unit 98 and the secondary boot sensor unit 120 on a paired channel, the corresponding left or right boot power indicator LED 174, 176 will blink continually. This informs the skier 10 that the system is sending and receiving signals. In alternative embodiments, in response to receiving a signal from the master boot sensor unit 98 and the secondary boot sensor unit 120, the hand controller unit 24 generates an audio output signal and sends this audio signal to the stereo audio jack 86.

Similarly, LED 174, 176 will blink at one specified rate to indicate satisfactory power is being supplied to the master boot sensor unit 98 or the secondary boot sensor unit 120 and will blink at a second specified rate to indicate that insufficient power is being supplied to each of the master boot sensor unit 98 and the secondary boot sensor unit 120. Such insufficient power may indicate that batteries 52, 53 of the master boot sensor unit 98 or the secondary boot sensor unit 120 need to be replaced. In the embodiment of FIG. 10, the first specified rate is a one second interval, and the second specified rate is a three second interval.

The receiver unit 170 includes one or more antennas 194 communicatively coupled to a receiver 170. The receiver receives a signal from the antenna 194 and communicates that signal to a demodulator 196. The demodulator 196 recovers the information content from the modulated signal received by the antenna 194. The demodulator 196 receives FM signals, demodulate left and right channels on a received carrier, and provide the demodulated signals to at least one operational amplifier (Op. Amp) 198. The Op. Amp 198 performs various functions on the signals received from the demodulator 196, including amplification, filtering, etc. The Op. Amp 198 then sends the modified signals to the control module 168. In some embodiments, the Op. Amp 198 may send the modified signals to the signal condition 188. It should be appreciated that the functions performed by the Op. Amp 198 may alternatively or in combination be performed by the signal condition 188. Such functions may include filtering, conversion of a signal from analogue to digital format, amplifying the signal, etc.

One or more antennas 194 include a monopole antenna. The antenna 194 includes a copper strip with a length corresponding to a fractional value of a desired frequency of the sport monitoring system. In the embodiment of FIG. 10, the antenna 194 is three eighths a wavelength of the operating frequency of the sport monitoring system. The sport monitoring system operates at a frequency of 904 MHz. One skilled in the art will readily recognize that other antenna designs, operating frequencies, and/or systems may implement the functionality of the antenna 194.

The user interface 172 includes a power switch 200 for powering on the system. Power switch 200 may correspond to the power button 66. The user interface 172 further includes a pressure sensitivity adjustor 202 and a proximity adjustor 204. The pressure sensitivity adjustor 202 may correspond to right and left pressure sensitivity adjustment buttons 72, 74 and 76, 78. Further, the proximity adjustor 204 may correspond to the simultaneous operation of the left sensitivity adjustment button 78 and the right sensitivity adjustment button 74.

The user interface 172 includes a volume adjustor 206. The volume adjustor 206 may correspond to the volume adjustment buttons 68, 70. The user interface 172 includes an indicator 208, which is configured to communicate sensor data to the skier 10 via earphones 26 through the stereo audio jack 86. Such sensor data includes a left notification signal and a right notification tone corresponding to a pressure value received from the corresponding master boot sensor unit 98 and secondary boot sensor unit 120 being below a set threshold value. Such sensor data further includes a proximity notification tone corresponding to the master boot sensor unit 98 and the secondary boot sensor unit 120 being outside of a set range of proximity of one another.

The control module 168 receives the sensor signals from the receiver unit 170, and controls the user interface 172 to provide one or more signals to the skier 10 indicating the current status of the output of the master boot sensor unit 98 and the secondary boot sensor unit 120. The user interface 172, for example, includes the indicator 208 that provides an audio interface with audio feedback to the skier 10 to indicate a status of the master boot sensor unit 98 and the secondary boot sensor unit 120 including pressure sensor and proximity sensor data. The skier 10, based on the audio feedback, may alter or adjust their use of equipment associated with the master boot sensor unit 98 and the secondary boot sensor unit 120 in order to make a turn in a more efficient manner or with enhanced technique. For example, the skier 10 upon hearing a tone indicating that insufficient pressure is being applied to the front of a left or right ski boot 12 may alter their position to apply additional pressure to the identified ski boot 12 and therefore be in a position to make a more efficient turn. Similarly, the skier 10 upon hearing a tone indicating that their skis 14 are too close together or too far apart as defined by a proximity range value, may take action to alter the spacing of the skis and therefore be in a position to make a more efficient turn.

Figure 11:
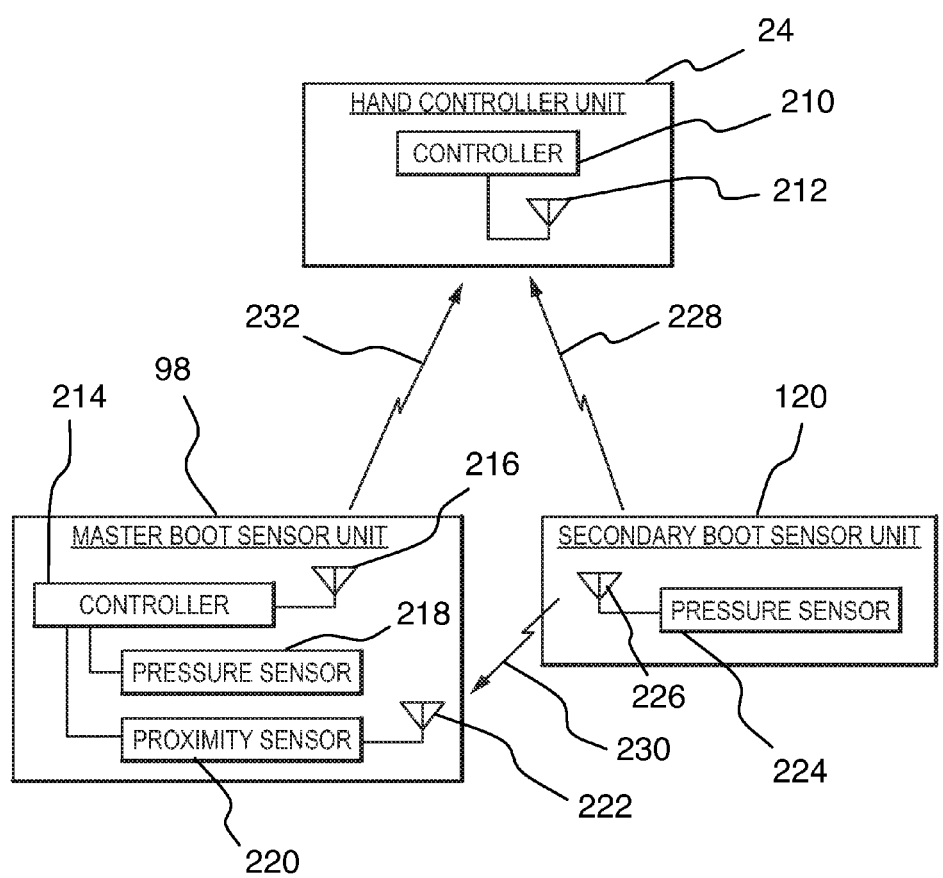
FIG. 11 is a schematic diagram of the communication links between the controller circuitry in the hand controller unit, the secondary boot sensor unit, and the master boot sensor unit.

With reference to FIG. 11, the transmission and reception among various components of the sports monitoring system of an exemplary embodiment is described. The system includes a left and a right boot sensor unit 20, 22 which, for ease of explanation, correspond to the master boot sensor unit 98 and the secondary boot sensor 120, and the hand controller unit 24. The hand controller unit 24 includes a controller 210, which may correspond to the control module 168, and a receiver 212, which may correspond to the receiver unit 170. The master boot sensor unit 98 includes a controller 214, which may correspond to the control module 100, a transmitter 216, which may correspond to the transmitter unit 102, a pressure sensor 218, which may correspond to the pressure sensor unit 104, a proximity sensor 220, which may correspond to the proximity sensor unit 106, and a proximity receiver 222, which may correspond to the combination of the proximity sensor unit 106 and the proximity antenna 108. The secondary boot sensor unit 120 includes a pressure sensor 224, which may correspond to the pressure sensor unit 146, and a transmitter 226, which may correspond to the transmitter unit 144.

The master boot sensor unit 98 transmits sensor data to the hand controller unit 24 on a first channel 232. The secondary boot sensor unit 120 transmits sensor data to the master boot sensor unit 98 on a second channel 226 and to the hand controller unit 24 on a third channel 228. In the embodiment of FIG. 11, the second channel 226 is the same as the third channel 228.

In alternative embodiments, the secondary boot sensor unit 120 may transmit different data on the second channel 226 and the third channel 228.

Figure 12:
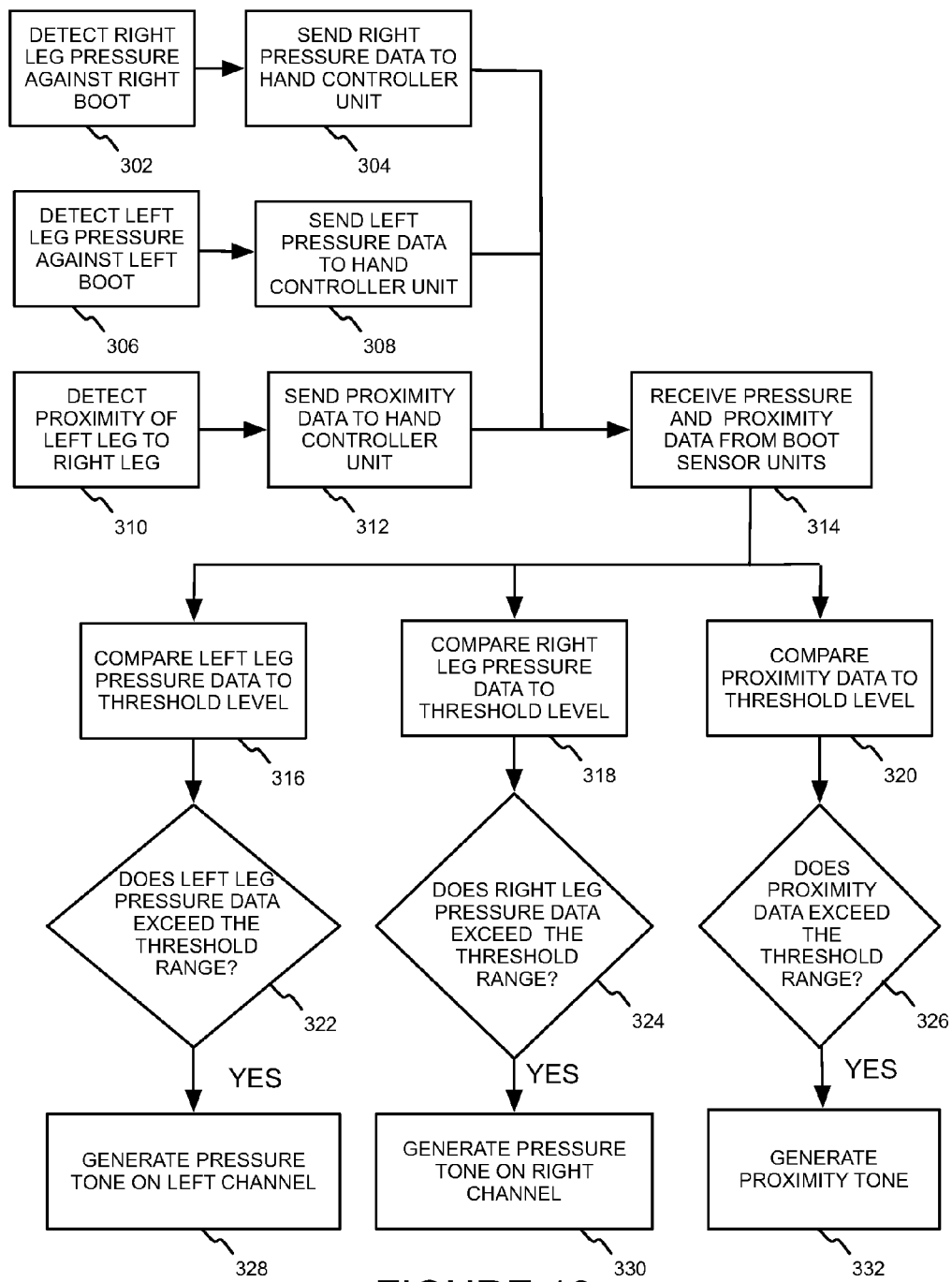
FIG. 12 is a flow chart of functions performed by the components of the sports monitoring system of FIG. 11.

With reference to FIG. 12, a block function diagram of some embodiments of a sports monitoring apparatus operation is described. Initially, the skier 10 powers on the hand controller unit 24 and each boot sensor unit 98, 120. In the embodiment of FIG. 12, the skier 10 powers on the hand controller unit 24, master boot sensor unit 98, and secondary boot sensor unit 120 in a predetermined order for correct operation. The skier 10 inserts the gas-filled bladders 30 extending a substantial vertical length into the ski boots 12 adjacent to the tongue 28 of the ski boots 12 and the skier shins, secures the ski boots 12 on the legs, and attaches the boots 12 to skis 14. The skier 10 takes a standing position with light forward pressure and adjusts the volume to a desired level using the volume adjustment buttons 68, 70. The skier 10 adjusts the right and left sensitivity adjustment controls 72, 74 and 76, 78 to the setting just beyond the point where the tone is silent. The skier 10 can adjust sensitivity of pressure feedback by applying different levels of pressure to the front of the ski boot 12 when adjusting the right and left sensitivity controls 72, 74 and 76, 78.

In alternative embodiments, one or more of the hand controller unit 24 and boot sensor units 98 and 120 may communicate wirelessly with another device to report sensor data, such as a mobile device of a coach or trainer, to better facilitate ski or other sports performance.

The gas pressure in the gas-filled bladder 30 increases and decreases based upon the pressure of the skier 10's shin compressing the gas-filled bladder 30. This change in pressure is detected 302, 306 and measured by the pressure sensor units 104, 146. A measured pressure value is communicated to 304, 308 and received at 314 by the hand controller unit 24. The hand controller unit 24 compares the pressure value to the threshold value 316, 318 set by the threshold setting of the sensitivity adjustment controls 72, 74 and 76, 78. If it is determined that the pressure value is outside the acceptable threshold range 322, 324 based on pressure reference value, a tone is generated 328, 330. This tone is output to the earphones 26 through a 3.55 mm stereo audio jack 86, alerting the skier 10 in real time that he is generating inadequate pressure to execute an efficient ski turn such that he can instantaneously adjust his form to generate sufficient pressure, silencing the tone.

The data sent from the boot sensor unit 98, 120 includes information that identifies whether the transmission is from the left boot sensor unit 20 or the right boot sensor unit 22. The hand controller unit 24 uses this information to generate a tone on the associated audio channel.

A skier 10 may activate a proximity detection function and set a proximity reference point and associated threshold range by placing the skis 14 a desired distance apart from one another and selecting a proximity set function on the hand controller unit 24. Once the proximity detection system is activated, the proximity sensor 220 detects the proximity of the limbs, limb portions or associated structures 310. The master boot sensor unit transmitter 124 sends proximity data to the hand controller unit 24 at 312, 314. The hand controller unit 24 compares the pressure data to the proximity reference point 320. If it is determined that the proximity value is outside the associated threshold range 326, a tone is generated 332. In the embodiment of FIG. 12, the proximity indication is an audio signal distinct from the pressure indication audio signals. The skier 10 receives real time proximity feedback via earphones 26.

Figure 13:
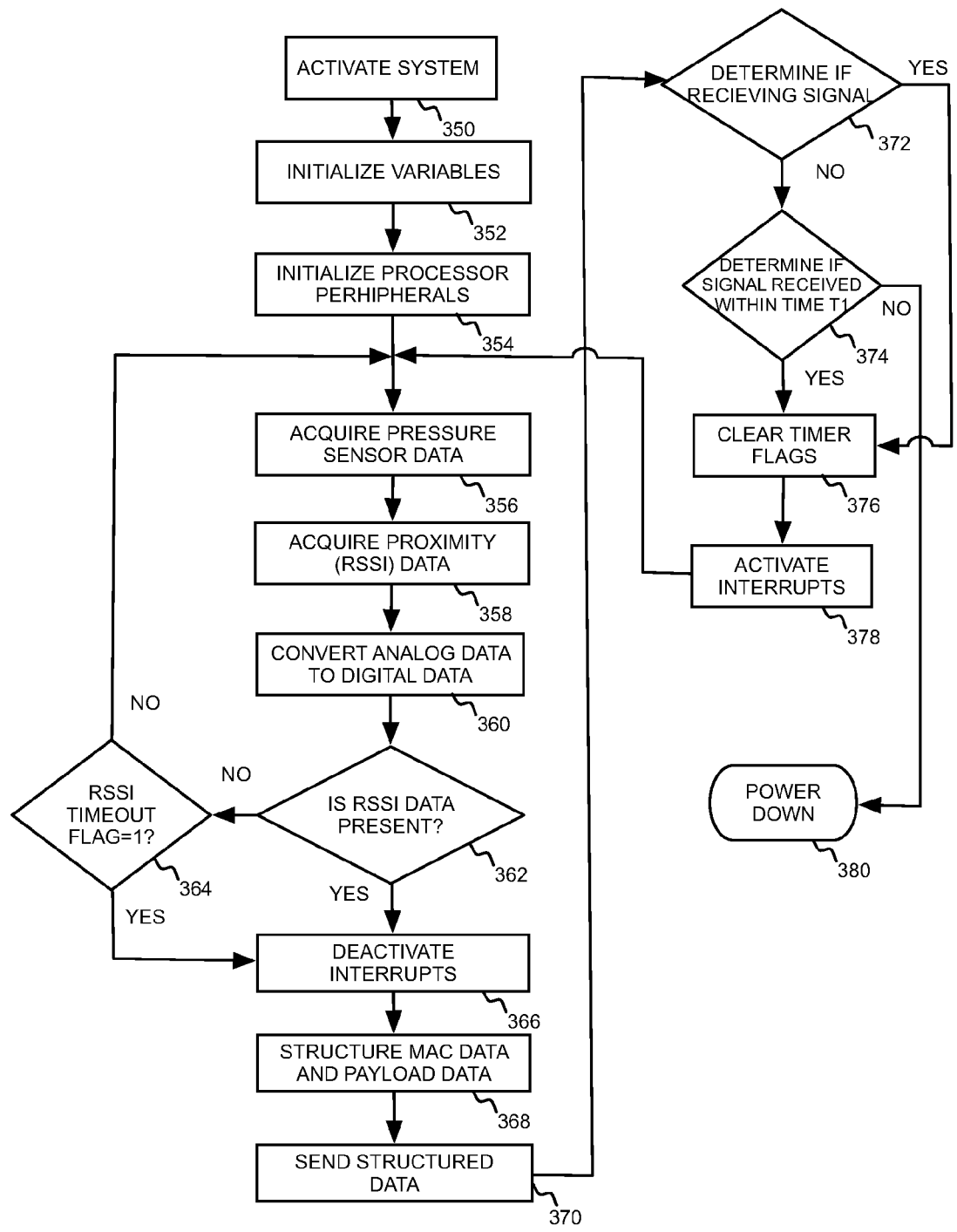
FIG. 13 is a flow chart of software process of the master boot sensor unit of the sports monitoring system of FIG. 11.

FIG. 13 schematically illustrates a master boot sensor unit software process methodology, according to some embodiments. When the master boot sensor unit 98 is activated, firmware variables and processor peripherals are initialized 350, 352, 354. Once initialization is complete, acquisition of pressure sensor data is initiated 356. The pressure sensor 218 produces a voltage output proportional to the absolute pressure. The analog output voltage produced by the sensor is a calculated voltage value, divided and lightly filtered, operable to prevent aliasing before being applied directly to an ADC channel of the microcontroller 214. The microcontroller 214 has embedded within itself components and features that provide an accurate 10/12 bit conversion of analog data at 1.1 MSPS rates. In the embodiment of FIG. 13, the voltage is a fairly stable DC output which enables the use of a 10 bit conversion and a conversion rate of about 20 KSPS.

Typically, the master and secondary boot sensor unit transmitters 124, 166 require approximately 20 mS to execute all the scheduled tasks assigned. In certain embodiments, during the period that the boot sensor unit transmitters 124, 166 are performing their tasks, and specifically with regard to the pressure sensor 218, 224, the microcontroller via the functions contained in the logic modules 110, 150 commands the pressure sensors 128, 164 to activate and subsequently provide a delay enabling the pressure sensors 128, 164 to stabilize. After this delay, the microcontrollers 100, 142 execute sixteen ADC sampling conversions of the pressure sensor output voltage and average these readings to provide recursive filtering. It should be clear to those skilled in the art that the number of sampling conversions can be higher or lower than sixteen.

The master boot sensor unit 98 includes a proximity receiver 132, and given that the secondary boot transmitter 120 may be in some degree of proximity to the master boot sensor unit 98 and its proximity receiver 132, as the degree of proximity varies, the level of RF power 109 received by the proximity receiver 132 will vary. The RF power received 109 by the proximity receiver 132 is converted to a DC signal 360 using an analog to digital converter that is configured to provide a RSSI level that is proportional to the degree of proximity between the master boot sensor unit 98 and the secondary boot sensor unit 120. The RSSI output can be a DC voltage sampled by the proximity sensor 106 at an approximate 50 mS rate.

The RSSI sampling process first determines if the signal is a valid transmitter signal. The secondary boot sensor unit transmitter 166 sends a series of synchronization pulses of known duration to the proximity sensor receiver 132, which is operable to discriminate between true system signal and noise based on the pulse timing. If the master boot sensor unit controller 214 determines that there is no valid RSSI data, it continues to loop through the data acquisition cycle for a defined period of time. If that period of time is exhausted, a timeout flag is set and the process will continue without RSSI data 364. If at any time valid RSSI data is acquired, the process proceeds without additional looping through the data acquisition cycle.

Once the proximity sensor receiver 132 determines the signal is a system signal, the master boot sensor controller 214 deactivates interrupts 366 and enters a loop, in which, it samples and performs two hundred and fifty five conversions of RSSI data that are then accumulated and averaged. This serves as a mild recursive filtering function. The averaged data is then passed to functions included in the master boot sensor unit controller logic modules 110 that integrate the data into a MAC data structure 368 as described below. It should be clear to those skilled in the art that the number of conversions can be higher or lower than two hundred and fifty five.

The MAC data structure provides a standard data structure whereby information can be passed to components within the sport monitoring apparatus. The MAC data structure further provides a means to uniquely identify systems and components as being distinct from other systems.

For example, in one or more embodiments, the MAC structure includes the following parameters:

a) 2 byte system level MAC ID that uniquely identifies a system;

b) 2 byte local device MAC ID that uniquely identifies a device to itself and the system, for example, as a left or right boot sensor unit transmitter 124, 126;

c) 2 byte remote device MAC ID;

d) 1 byte command code indicating to the receiver to direct the execution of events;

e) 2 bytes of data representing data received from a given pressure sensor 218, 224 or proximity receiver 132; and f) 1 byte checksum demonstrating the data is valid and has not been corrupted during transmission.

The data is then communicated to the hand controller unit 24 for processing and event execution.

The hand controller unit 24 monitors and determines if at least one boot sensor unit 98, 120 is sending a sensor feedback signal 372. If a signal is currently being received, or has been received within a predetermined time T, the hand controller unit 24 remains powered on. If the hand controller unit 24 has not received any sensor signals in a predetermined amount of time T, the hand controller unit 24 may power down. In some embodiments, T is approximately ten minutes. It should be clear to one skilled in the art that T can consist of time periods other than ten minutes.

A similar operation can be used for each boot sensor unit 98, 120 once powered on. If the boot sensor unit 98, 120 is receiving feedback from at least one boot sensor unit 372, or has received such feedback in a predetermined time T1 374, then the boot sensor unit 98, 120 completes its cycle by clearing one or more timer flags 376 and reactivating interrupts 378. If the boot sensor unit 98, 120 has not received sensor feedback within a predetermined time T1 374, then the boot sensor unit 98, 120 powers down 380. It should be appreciated that other signals or power switching approaches may be used.

If the system is powered on, the hand controller unit 24 checks for pressure feedback signals. If the pressure feedback received from the at least one boot sensor unit 20, 22 is outside the associated threshold range set by the skier 10, then a pressure indication signal is generated. A left pressure feedback signal corresponds to a left indication signal, and a right pressure feedback signal corresponds to a right indication signal. The indication signal or signals may be audio tones communicated to each ear of the skier 10 via earphones 26.

Figure 14:
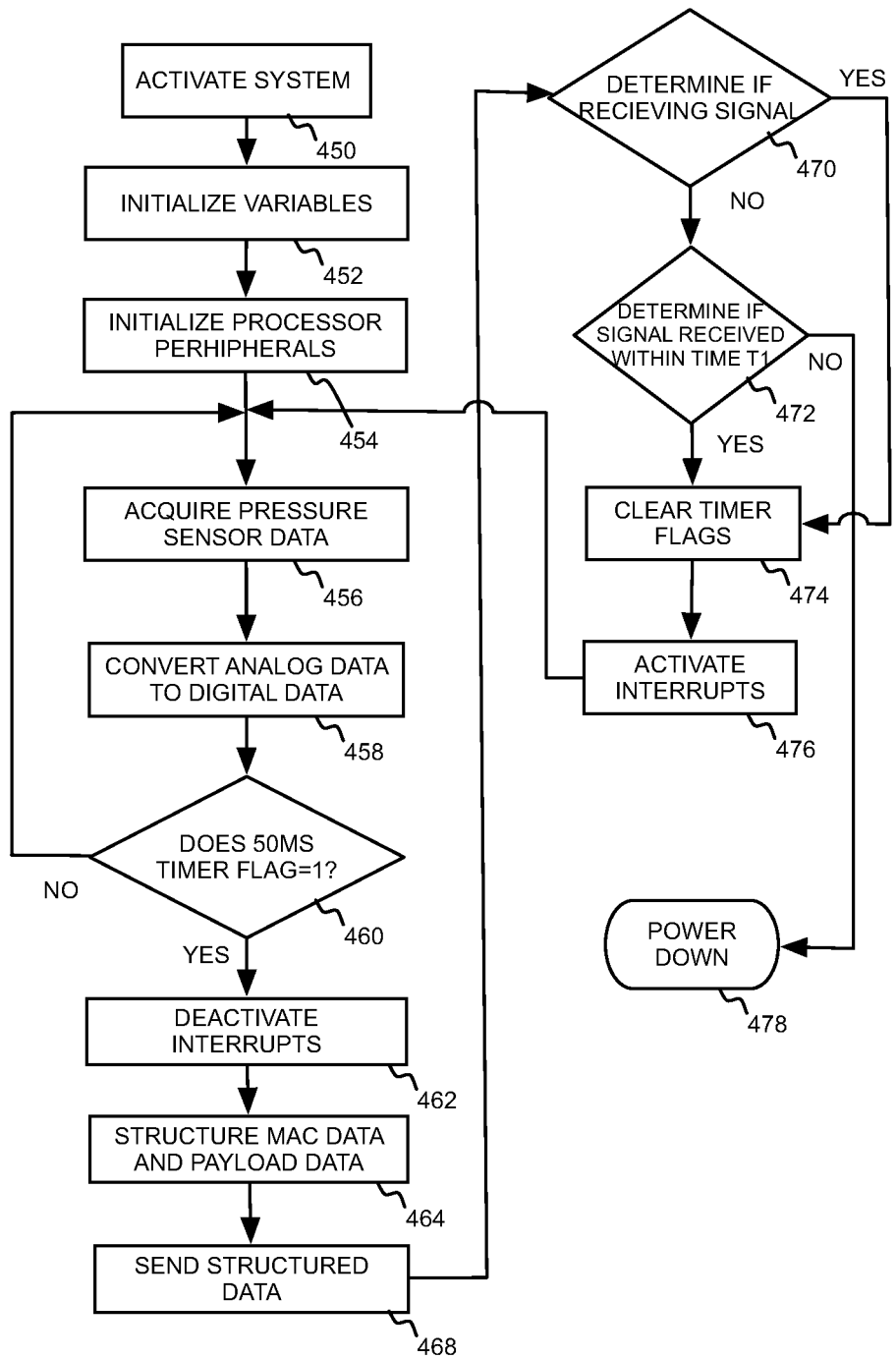
FIG. 14 is a flow chart of the software process of the secondary boot sensor unit of the sports monitoring system of FIG. 11.

FIG. 14 schematically illustrates a secondary boot sensor unit software process methodology, according to some embodiments. The secondary boot sensor unit process methodology differs from the master boot sensor unit process by excluding RSSI-related activity.

The software associated with the secondary boot sensor unit transmitter 166 includes a 50 mS timer scheduling the execution of all peripheral functions including acquiring pressure sensor data 456 and the communication of data 468. The firmware associated with the master boot sensor unit transmitter 124 is synchronous to the secondary boot sensor unit 166 transmitter as described below.

If the master boot sensor unit 98 includes a proximity sensor 220, it operates in a synchronous transmission mode in relation to the transmission timing of the secondary boot sensor unit 120. The secondary boot sensor unit 120 transmits data every 50 mS. The master boot sensor unit 220 includes a proximity receiver 132 that detects the signal 109 transmitted from the secondary boot sensor unit 120, and uses the detection of said signal as a trigger to schedule transmission times for master boot sensor unit data. This is approximately 25 mS after the secondary boot sensor unit transmitter 166 has initiated its transmission of data. By having the two transmitters 124, 166 synchronized to one another, the probability of data collisions as between the two transmitters is reduced.

In some embodiments, the master boot sensor unit 98 is not equipped with a proximity sensor 220, or the proximity receiver 132 fails to detect a signal from the secondary boot sensor unit transmitter 166. In either of these two cases, the system may use an asynchronous operating mode whereby both the secondary boot sensor unit 120 and the master boot sensor unit 98 transmit every 50 mS, plus or minus a random delay of a few mS. This random delay is generated by a random delay generator algorithm.

Figure 15A:
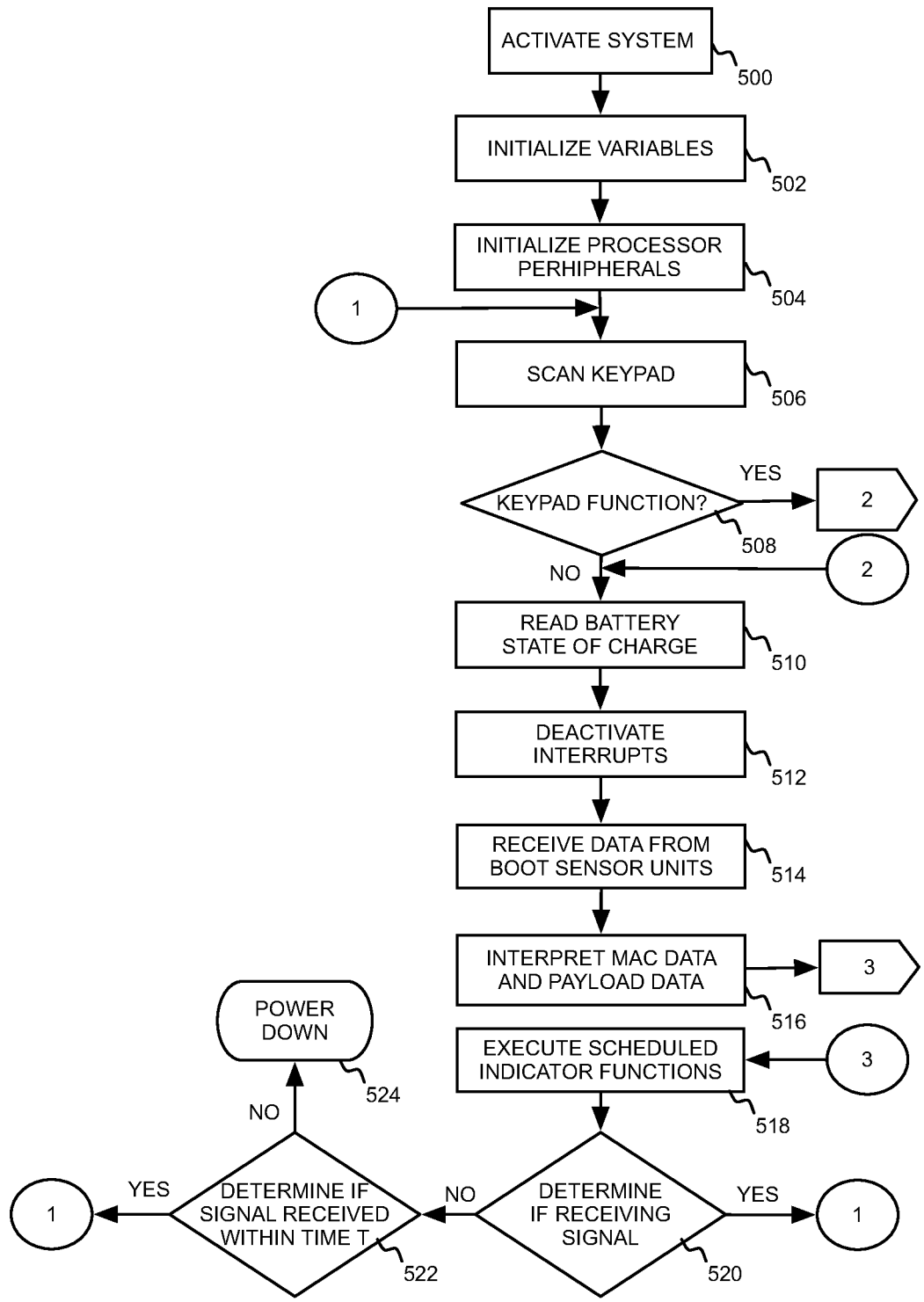
FIGS. 15A, 15B, and 15C is a flow chart of the software process of the hand controller unit of the sports monitoring system of FIG. 11.
Figure 15B:
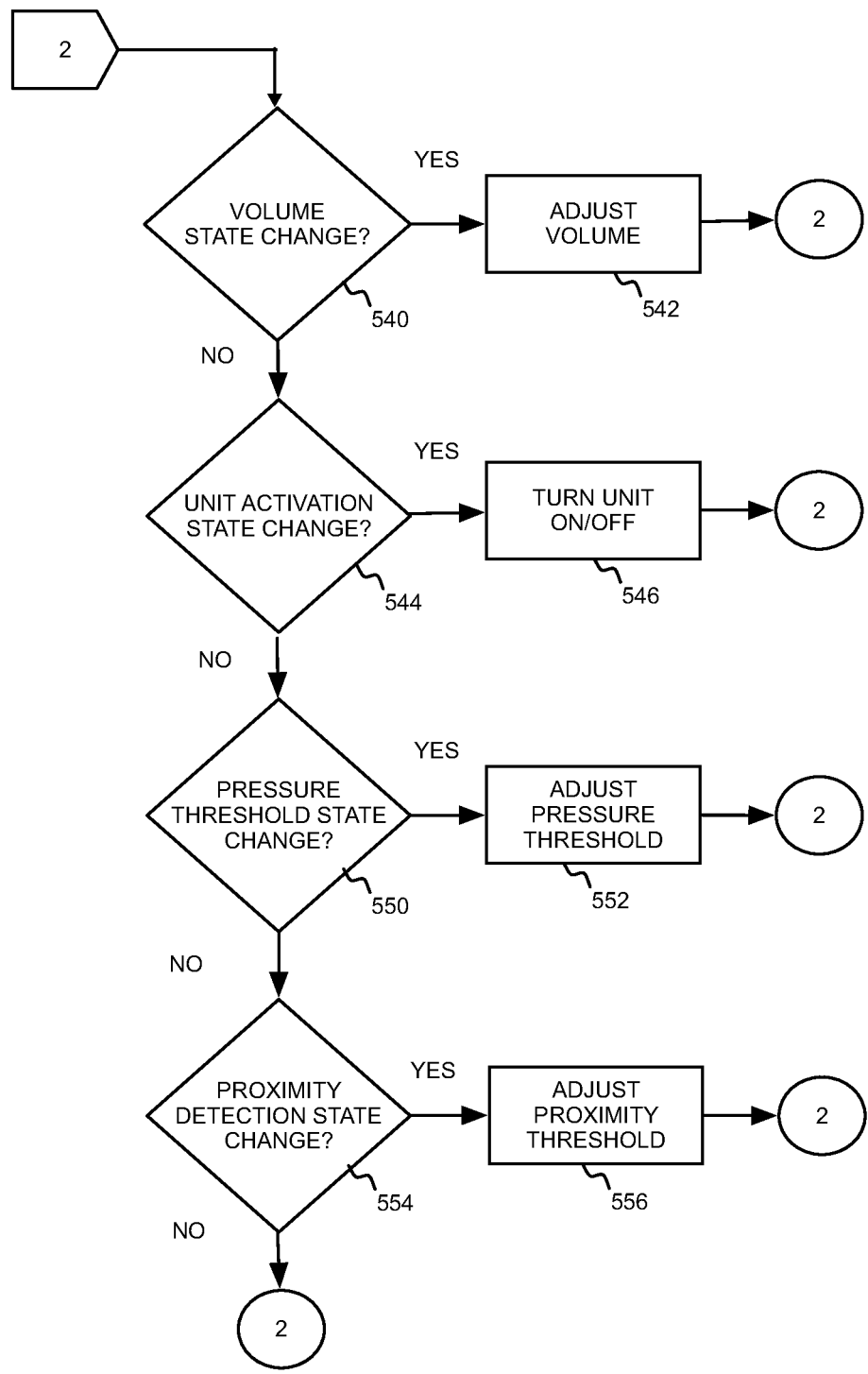
Figure 15C:
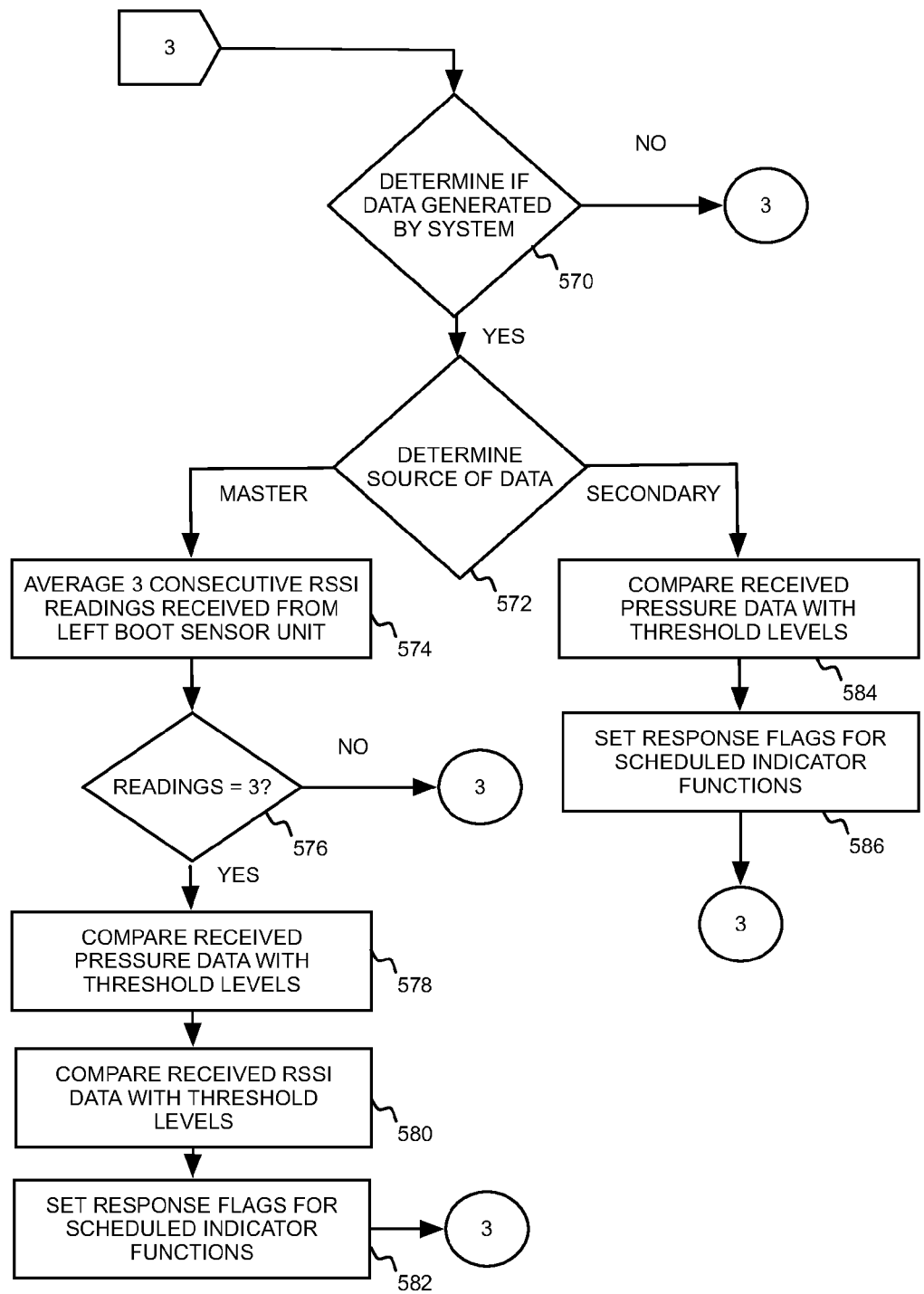

FIGS. 15A-15C schematically illustrate a hand controller unit software process methodology, according to some embodiments. When the system is activated, firmware variables and processor peripherals are initialized 500, 502, 504. Once initialization is complete, the keypad is scanned for the occurrence of any activity 506. If it is determined that there is keypad activity indicating a function should be performed, the hand controller unit evaluates the state of the associated variables indicating what functions should be scheduled. For example, if there is a state indicating a volume change has occurred 540, the value is assessed and the volume adjustment function is scheduled 542. If there is a state indicating the activation state of the unit has changed 544, it is assessed and the apparatus is either powered on or powered off 546. If there is an indication that the pressure threshold state has changed 550, the event is scheduled and the pressure threshold set accordingly when the event is executed 552. If there is an indication that the proximity threshold should be changed 554, the event is scheduled and the proximity threshold is set accordingly when the event is executed 556.

Once any functions initiated by keyboard activity are scheduled, the state of the battery charge is determined and reported to the user 510. Interrupts are deactivated to avoid disruptions during receipt of transmission that might otherwise compromise the data being received 512. As the data is received from one or more boot sensor units 98, 120, the Mac data structures are parsed for analysis 516.

The Mac data structure is parsed and the system level MAC ID value is evaluated. If it is determined that the data originated from the same system 570, then the local device MAC ID value is assessed to determine which component in the system was the source of the data 572. If the local MAC ID indicates the source of the data was the secondary boot sensor unit 120, the data is compared to the pressure threshold reference point as discussed previously 584, and the response flags for any required scheduled user indicator functions are set 586.

If it is determined that the source of the data is the master boot sensor unit 98, one or more additional processes are invoked to receive, process and analyze the RSSI data. The payload RSSI data for three consecutive readings are averaged and compared to the threshold reference point 574, 576, 580, and response flags for any required scheduled user indicator functions are set 582. It should be appreciated by one skilled in the art that the number of readings averaged can be more or less than three.

With reference to all of the figures above, a method for monitoring pressure of limbs or portions of limbs against pieces of equipment and the proximity of the respective limbs or portions of limbs, followed by instantaneous feedback to the user with respect to the status of pressure and proximity thresholds is described. The example used to illustrate this embodiment will be that of a ski training device used in conjunction with ski boots, but applications to other sports and activities are also suggested, such as use with boarding boots, motorcycle boots, water skiing boots, wake boarding boots, and other boots.

In a first step of an exemplary embodiment wherein a gas-filled pressure sensor is used, the gas pressure in the bladder is normalized to the ambient air pressure.

In a next step, the gas-filled bladder assumes its natural shape.

In a next step, the boot sensor units are inserted into the corresponding right or left ski boot such that the bottom of the boot sensor unit casing rests within the area one inch directly above the upper most point of the boot tongue.

In a next step, the hand controller unit is activated. An LED blinks continuously, or at a one second interval, indicating that the hand controller unit is powered on. A second LED on the hand controller unit indicates that a transmission is being received from a first pressure sensor. A third LED on the controller indicates that a transmission is being received from a second pressure sensor.

In a next step, proximity detection is activated by toggling an activation switch on the hand controller unit. Alternatively, other switching mechanisms may be used, such as pressing and holding two of the pressure adjustment buttons simultaneously for a set duration of time.

In a next step, the skier attaches a pair of skis to the skier's boots.

In a next step, the skier inserts a device capable of generating stereo sound into the stereo jack on the wireless controller.

In a next step, the skier is to assume an erect posture and neutral stance where there is no pressure against gas filled bladder inserted into the ski boot.

In a next step, a soft tone is generated on the left and the right stereo channels. Tone volume for the right channel may be adjusted to a desired level through the use of one or more buttons on the hand controller unit. Tone volume for the left channel may be adjusted to a desired level through the use of one or more buttons on the on the hand controller unit.

In a next step, the skier may lean in the skis to a sufficient degree to create a light pressure against the gas-filled bladder.

In a next step, the skier may adjust the sensitivity threshold for the right channel to a setting immediately beyond the point where the tone stops in the right ear.

In a next step, the skier may adjust the sensitivity threshold for the left channel to a setting immediately beyond the point where the tone stops in the left ear.

In a next step, the wireless controller powers down in a set number of minutes if either the wireless controller does not receive a stream of pressure data or if there is no transmission received.

In a next step, the boot sensor may powers down in a set number of minutes if there is no detectable change in pressure.

In a next, a distinct tone is generated on one or more channels if the proximity of the boot sensor unit is outside a range associated with a proximity reference point.

Also, contemplated herein are methods for connecting various components of a sport performance monitoring apparatus. The methods thus encompass the steps inherent in the above described mechanical structures and operation thereof.

While certain embodiments and details have been included herein for purposes of illustrating aspects of the instant disclosure, it will be apparent to those skilled in the art that various changes in systems, apparatus, and methods disclosed herein may be made without departing from the scope of the instant disclosure.

The invention claimed is:

1. A boot pressure monitoring system comprising:
 a controller comprising a left boot pressure sensor input communicable with a left boot pressure indicator and a right boot pressure sensor input communicable with a right boot pressure indicator, the left boot pressure indicator comprising a left boot pressure audio output and a left earphone, and the right boot pressure indicator comprising a right boot pressure audio output and a right earphone;
 a left flexible boot pressure sensor communicable with the left boot pressure sensor input;
 a right flexible boot pressure sensor communicable with the right boot pressure sensor input, wherein each flexible boot pressure sensor comprises a flexible bladder with an interior, material-container compartment, and a pressure sensor communicable with the flexible bladder;
 a boot proximity sensor;
 a boot proximity sensor indicator communicable with the boot proximity sensor, the boot proximity sensor indicator comprising a proximity audio output communicable with at least one of the left and right earphones; and the controller further comprising a proximity adjuster communicable with the boot proximity sensor indicator.

* * * * *